(12) United States Patent
Uesugi et al.

(10) Patent No.: US 7,476,213 B2
(45) Date of Patent: Jan. 13, 2009

(54) METHOD AND SYSTEM FOR SUPPLYING GAS INTO A BODY

(75) Inventors: Takefumi Uesugi, Tokyo (JP); Daisuke Sano, Tokyo (JP); Yoshimine Kobayashi, Tokyo (JP); Mutsumi Ohshima, Tokyo (JP); Takehiro Nishiie, Tokyo (JP); Atsuhiko Kasahi, Yokohama (JP); Kenji Noda, Tokyo (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 11/174,251

(22) Filed: Jul. 1, 2005

(65) Prior Publication Data

US 2006/0004322 A1 Jan. 5, 2006

(30) Foreign Application Priority Data

Jul. 1, 2004 (JP) ............................. 2004-196064

(51) Int. Cl.
*A61M 37/00* (2006.01)
(52) U.S. Cl. .................... 604/26; 600/101; 600/153
(58) Field of Classification Search ................ 600/153, 600/156, 178, 160, 158, 159; 604/26, 23; 128/204.18, 205.11, 205.24, 207.16
See application file for complete search history.

(56) References Cited

U.S. PATENT DOCUMENTS 5,139,478 A * 8/1992 Koninckx et al. ............. 604/26
5,246,419 A * 9/1993 Absten ........................ 604/26
5,549,546 A * 8/1996 Schneider et al. ............. 604/26
5,632,740 A * 5/1997 Koch et al. ................. 362/554
6,142,147 A * 11/2000 Head et al. ............. 128/204.21
6,148,816 A * 11/2000 Heinonen et al. ...... 128/205.24
6,354,294 B1 * 3/2002 Villareal, Jr. ........... 128/204.18
6,428,500 B1 * 8/2002 Koninckx ..................... 604/26
2005/0010164 A1 * 1/2005 Mantell ........................ 604/26

FOREIGN PATENT DOCUMENTS

| JP | 8-256972 | 10/1996 |
| JP | 2000-139823 | 5/2000 |
| JP | 2000-139830 | 5/2000 |

* cited by examiner

*Primary Examiner*—Nicholas D Lucchesi
*Assistant Examiner*—Christopher D Koharski
(74) *Attorney, Agent, or Firm*—Ostrolenk, Faber, Gerb & Soffen, LLP

(57) ABSTRACT

In a gas supply system, a selection unit is configured to send an instruction to select any one of first gas and second gas. In the gas supply system, a controller is operative to control at least one of a first gas supply unit for supplying the first gas and a second gas supply unit for supplying the second gas to selectively insufflate any one of the first gas and second gas into a body based on the instruction sent from the selection unit.

24 Claims, 18 Drawing Sheets

METHOD AND SYSTEM FOR SUPPLYING GAS INTO A BODY

CROSS REFERENCE TO RELATED APPLICATION

This application is based upon the prior Japanese Patent Application 2004-196064 filed on Jul. 1, 2004 and claims the benefit of priority therefrom so that the descriptions of which are all incorporated herein by reference.

BACKGROUND OF THE INVENTION

1. Field of the Invention

The present invention relates to a method and a system for supplying gas into a body.

2. Description of the Related Art

In recent years, laparoscopic surgeries have been practiced extensively. The laparoscopic surgery is executed for treating a patient with minimally invasive capability.

Specifically, in the laparoscopic surgeries, for example, a rigid endoscope, referred to as "rigidscope", for observation is inserted into a body cavity, such as, an abdominal cavity of a patient. A treatment tool is inserted into the abdominal cavity to be guided to a site to be treated therein while an image of the inside of the abdominal cavity, which is obtained by the rigidscope, is observed.

In such a laparoscopic surgery, an insufflator has been used for supplying carbon dioxide gas (hereinafter also referred to as $CO_2$) as insufflating gas into an abdominal cavity of the patient to ensure the rigidscope field and a space to manipulate the treatment tool.

Conventionally, some types of insufflators each for supplying carbon dioxide into one of body cavities, such as an abdominal cavity of the patient, have been prepared.

For example, Japanese Unexamined Patent Publication No. 2000-139830 discloses a gas supplying apparatus designed to feed a control signal to a pressure-regulating valve when gas flow volume does not reach a predetermined value. The control signal causes the pressure-regulating valve to increase the pressure of the output gas to control the amount thereof, thereby keeping an internal pressure of a living body at the predetermined value.

Moreover, Japanese Unexamined Patent Publication No. 8-256972 discloses an insufflator having a plurality of electro magnetic valves for controlling a state of gas flowing through a gas delivery channel extending from a gas supply source to an insufflation tool. Specifically, the insufflator is designed so that the plurality of electro magnetic values is integrated with a manifold valve, allowing the gas-flow state controlling section to become compact.

Japanese Unexamined Patent Publication No. 2000-139823 discloses an insufflator configured to insufflate air into a lumen of a patient and to keep the pressure inside the lumen constant.

In the meanwhile, when diagnosing and treating a lumen, such as the stomach, the large intestine, or the like of a patient as one of the body cavities thereof, a flexible endoscope, referred to as "flexiblescope", and a treatment tool therefor have been used. The flexiblescope has one thin and flexible end portion to be used as an access site into the lumen. The treatment tool for the flexiblescope is designed so that its forceps channel is inserted into the flexiblescope to project through an opening formed in the head of the one end portion of the flexiblescope.

When executing curative intervention, such as diagnosis and treatment of a lumen in a patient under such monitored conditions with the flexiblescope, in some cases, gas for lumens is injected into the lumen. The injection of gas aims at securing the flexiblescope field and a space to manipulate the treatment tool.

In these cases, the gas to be supplied into the lumen (organ cavity) can be transferred with a gas supply pump. As the gas for lumens, air has been generally applied, but carbon dioxide gas can be used.

Recently, as a new attempt, in the laparoscopic surgeries, the rigidscope is inserted into an abdominal cavity of a patient with the flexiblescope inserted into a lumen of the patient. This allows identification of a site to be treated in the patient based on an image of the inside of the abdominal cavity, which is obtained by the rigidscope, and that of the inside of the lumen, which is obtained by the flexiblescope.

Under such monitored conditions with both the rigidscope and flexiblescope, in some cases, for example, air as gas for lumens is injected through the flexiblescope into the lumen so that the lumen inflates.

When air is supplied into the lumen, it is difficult for the air to be absorbed into the living body. This may cause the lumen to remain inflated.

For this reason, when inserting the rigidscope into an abdominal cavity of a patient while inserting the flexiblescope into a lumen thereof, using an endoscope $CO_2$ regulator (hereinafter referred to as ECR) has been considered to supply carbon dioxide gas ($CO_2$), which is absorbed easily into the living body, into the lumen.

SUMMARY OF THE INVENTION

The present invention has been made on the background.

According to one aspect of the present invention, there is provided a gas supply system including a first gas supply unit configured to supply first gas into a body and a second gas supply unit configured to supply second gas into the body. The gas supply system includes a selection unit configured to send an instruction to select any one of the first gas and the second gas, and a controller electrically connected to the first gas supply unit, the second gas supply unit, and the selection unit. The controller is operative to control at least one of the first gas supply unit and the second gas supply unit to selectively insufflate any one of the first gas and second gas into the body based on the instruction sent from the selection unit.

According to another aspect of the present invention, there is provided a gas supply system. The gas supply system includes means for supplying first gas into a body, means for supplying second gas into the body, and means for sending an instruction to select any one of the first gas and the second gas. The gas supply system includes means for selectively insufflating any one of the first gas and second gas into the body based on the instruction sent from the selection means.

According to a further aspect of the present invention, there is provided a method of supplying gas into a body. The method includes supplying first gas into a body, supplying second gas into the body, sending an instruction to select any one of the first gas and the second gas, and selectively insufflating any one of the first gas and second gas into the body based on the instruction sent from the sending step.

BRIEF DESCRIPTION OF THE DRAWINGS

Various aspects of the present invention will be more particularly described with reference to the accompanying drawings in which.

DETAILED DESCRIPTION OF EMBODIMENTS OF THE INVENTION

Various embodiments according to the present invention are described with reference to the accompanying drawings.

First Embodiment

Figure 1:
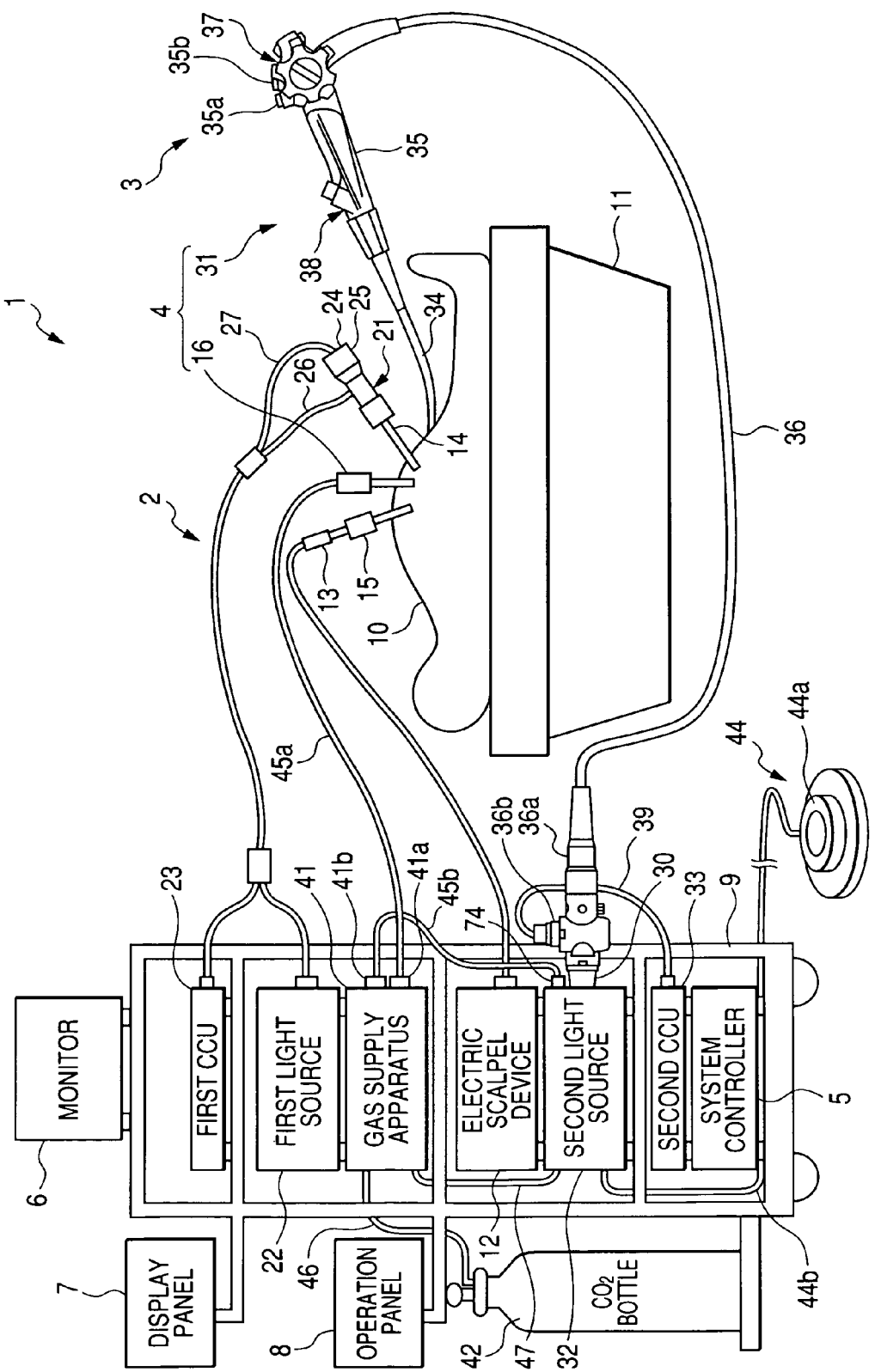
FIG. 1 is an overall structural view schematically illustrating the structure of an endoscopic surgical system equipped with a gas supply system according to a first embodiment of the present invention.

As shown in FIG. 1, a laparoscopic surgery system, referred to as a surgical system hereinafter, 1 has a first endoscope system 2, a second endoscope system 3, and a gas supply system 4 according to an embodiment of the present invention. The gas supply system 4 has a gas supply apparatus 41 and a third trocar 16, and includes a flexible endoscope 31 and a second light source 32.

The surgical system 1 has a system controller 5, a monitor 6 as a display device, a center display panel 7, a center operation panel 8, and a movable cart (trolley) 9.

Reference numeral 10 designates a patient (body), and reference numeral 11 designates an operation table that allows the patient 11 to lie thereon. Reference numeral 12 designates an electric scalpel device as an example of operation devices, which is mounted on the cart 9. The surgical system 1 has an electric scalpel 13 serving as an operation tool. The electric scalpel 13 is electrically connected to the electric scalpel device 12.

Reference numerals 14, 15, and 16 designate first, second, and third trocars, which are inserted into, for example, an abdominal portion of the patient 10, respectively. The first trocar 14 allows an endoscope, described herein after, of the first endoscope system 2 to be guided into a first body cavity, such as an abdominal cavity AC (see FIG. 3) of the patient 10. The abdominal cavity AC, which means a cavity separated by the diaphragm from the thoracic cavity above and by the plane of the pelvic inlet from the pelvic cavity below, serves as a first body cavity of the patient 10 according to the first embodiment.

The second trocar 15 permits guide of a treatment tool into the abdominal cavity AC. The treatment tool, such as the electric scalpel 13, is operative to remove and/or treat a tissue corresponding to at least one site to be treated in the abdominal cavity AC.

The third trocar 16 allows gas for the abdominal cavity, such as carbon dioxide gas, to be introduced into the abdominal cavity AC. The carbon dioxide gas, referred to as "$CO_2$" can be easily absorbed into a living body, such as the patient 10, which is supplied from the gas supply system 4. The carbon dioxide gas can be introduced into the inside of the abdominal cavity AC through at least one of the trocars 14 and 15.

The first endoscope system 2 includes a rigid endoscope 21 as a first endoscope with, for example, a rigid insert portion at one end thereof. The rigid endoscope 21 is referred to as "rigidscope" hereinafter. The first endoscope system 2 includes a first light source 22, a first camera control unit, referred to as "first CCU" hereinafter, and a camera (TV camera) for endoscopes.

One end portion of the insertion portion (not shown) of the rigidscope 21, for example, is configured to be inserted in part into the first trocar 14. The rigidscope 21 is provided with an illumination optics (not shown) and an observation optics (not shown), which are installed in the one end portion of the insertion portion. The illumination optics is composed of, for example, a light guide and the like, and configured to illuminate light onto a target, such as the site to be treated, inside the patient 10. For example, the observation optics is composed of relay lenses and the like. The observation optics is configured to optically deliver an optical image of the target illuminated by the light.

The rigidscope 21 is provided at the other end side of the insertion portion with an eyepiece 25 that allows an operator to observe the optical image delivered by the observation optics. The camera 24 is detachably installed in the eyepiece 25. The camera 24 is integrated with an image pickup device, such as a CCD (Charge Coupled Device) or the like, having a light sensitive pixel area, wherein the optical image delivered by the observation optics is focused on the light sensitive pixel area thereof. The optical image of the target focused on the light sensitive pixel area of the image pickup device is photoelectrically converted into an electric signal as a first image signal, by the image pickup device.

The first endoscope system 2 is provided with a light guide cable 26 extending from one side of the other end of the rigidscope 21. The light guide cable 26 is optically coupled to the first light source 22, allowing optical coupling between the rigidscope 21 and the first light source 22. The first endoscope system 2 is provided with an image pickup cable 27 electrically connecting between the first CCU 23 and the camera 24.

The first light source 22 has a function of supplying illumination light to the illumination optics of the rigidscope 21 via the light guide cable 26. The first CCU 23 is operative to execute electrical drive control of the image pickup device of the camera 24. When the first image signal corresponding to the optical image of the target, which is picked up by the image pickup device, is sent to the first CCU 23, the first CCU 23 is operative to receive the first image signal to subject the received first image signal to image processing of necessity. The first CCU 23 is operative to output the image-processed first image signal to at least one of the monitor 6 and the center display panel 7.

These operations allow at least one of the monitor 6 and the center display panel 7 to display a first image of the target thereon based on the first image signal. That is, the first image is an endoscopic image corresponding to the first image signal picked up by the rigidscope 21.

The second endoscope system 3 includes the flexible endoscope 31 as a second endoscope with, for example, a flexible insert portion 34 at one end thereof. The flexible insert portion is so flexible that it can be inserted into a lumen BC (see FIG. 3) as a second body cavity of the patient. In the specification, the lumen is defined as the cavity of an organ in a patient, such as the cavity of the stomach, the cavity of the large intestine, the cavity of a blood vessel, or the like in the patient. The flexible endoscope 31 is referred to as "flexiblescope" hereinafter. The second endoscope system 3 includes the second light source 32, and a second CCU 33.

The flexiblescope 31 has a substantially hollow-rod (tubular) shape, which is narrow in diameter and flexible. The flexiblescope 31 is internally formed with a gas delivery channel.

Specifically, the flexiblescope 31 is provided at its one end with the insert portion 34 to be inserted at its one end into the interior of the lumen BC, and a manipulator 35 whose one end is joined to the other end of the insert portion 34. The manipulator 35 allows, for example, an operator to manipulate the flexiblescope 31. The flexiblescope 31 is provided with a universal cord 36 whose one end is joined to the other end of the manipulator 35.

The manipulator 35 is provided with a gas and water supply switch 35a mounted thereon. The gas and water supply switch 35a is formed with a through hole, also referred to as "gas and water supply channel), communicated with the gas delivery channel inside the manipulator 35. The gas and water supply switch 35a, the gas delivery channel, and the insert portion 34 allow the operator to supply gas and water therethrough.

It should be noted that the term "operator" through the specification is not necessarily limited to a person who actually treats; the term "operator" refers to a concept that involves any of nurses or other operators who assist such a treatment action.

The manipulator 35 is provided with a suction switch 35b disposed thereto and a flexion knob 37 that allows the operator to flex a flexible portion (not shown) of the flexiblescope 31. The flexiblescope 31 is provided with a treatment tool insertion opening 38 formed to be communicated with the treatment tool channel (not shown) communicated with the gas delivery channel. The treatment tool insertion opening 38 allows treatment tools to be inserted therethrough. The other end of the universal cord 36 is coupled to a light source connector 36a optically detachably so that the universal cord 36 is optically coupled to the second light source 32 through the light source connector 36a.

The second light source 32 has a connector 30 so that the universal cord 36 is optically coupled to the connector 30 through the light source connector 36a.

Specifically, the second light source 32 has a function of supplying illumination light to the flexiblescope 31 through the connector 30, the light source connector 36a, and the universal cord 36.

The flexiblescope 31 is provided at its one end of the insertion portion 34 with an illumination optics. The illumination optics is composed of a light guide (not shown) that can illuminate light on a target inside the patient 10, such as the lumen BC, through an illumination window disposed to one side of the one end of the insertion portion 34.

The flexiblescope 31 is provided with an image pickup device, such as a CCD (Charge Coupled Device) or the like, installed in the one end of the insertion portion 34. The image pickup device has a light sensitive pixel area. The image pickup device is so arranged that an optical image of the target illuminated by the light outputted from the illumination optics is focused on the light sensitive pixel area of the image pickup device.

The second light source 32 is configured to insufflate air, which is supplied from a second air supplier, described hereinafter, to the flexiblescope 31 through the universal cord 36. The second light source 32 is coupled to the gas supply apparatus 41 of the gas supply system 4. The second light source 32 allows insufflation of the flexiblescope 31 with the carbon dioxide gas supplied from the gas supply apparatus 41. Specifically, the second light source 32 serves as part of the gas supply system 4.

The image pickup device of the flexiblescope 31 is electrically connected to the second CCU 33 through the universal cord 36 and the like. Reference numeral 39 is an electric cable electrically connecting between an electric connector 36b attached to the light source connector 36a and the second CCU 33.

The image pickup device is operative to photoelectrically convert the optical image of the target focused on the light sensitive pixel area into an electric signal as a second image signal.

The second CCU 33 is operative to execute electrical drive control of the image pickup device. When the second image signal corresponding to the optical image of the target, which is picked up by the image pickup device, is sent to the second CCU 33 through the electric cable 39, the second CCU 33 is operative to receive the second image signal to subject the received first image signal to image processing of necessity. The second CCU 33 is operative to output the image-processed second image signal to at least one of the monitor 6 and the center display panel 7.

These operations allow at least one of the monitor 6 and the center display panel 7 to display a second image of the target thereon based on the second image signal. That is, the second image is an endoscopic image corresponding to the second image signal picked up by the flexiblescope 31.

Turning now to the gas supply system 4, it includes the second light source 32, the gas supply apparatus 41, and a carbon dioxide gas cylinder ($CO_2$ bottle) 42 as a supplier. The gas supply system 4 has a foot switch 44 serving as an operation switch for controlling supply of the carbon dioxide gas into the lumen BC, an abdominal cavity tube 45a, and a lumen tube 45b. The $CO_2$ bottle 42 stores carbon dioxide in liquid.

The gas supply apparatus 41 is provided with a first adapter (connector) 41a for insufflation of the abdominal cavity AC and a second adapter 41b for insufflation of the lumen BC. The first adapter 41a is airtightly coupled to one end of the abdominal cavity tube 45a. The other end of the abdominal cavity tube 45a is airtightly coupled to the third trocar 16.

The second adapter 41b is airtightly coupled to one end of the lumen tube 45b. The other end of the lumen tube 45b is airtightly coupled to a $CO_2$ inlet adapter 74, described hereinafter, of the second light source 32.

The foot switch 44 is provided with a switch portion 44a and is configured to provide instructions to instruct supply of the carbon dioxide gas into the lumen BC to the second light source 32 while the operator or the like depresses the switch portion 44a with operator's foot or the like.

The gas supply apparatus 41 and the $CO_2$ bottle 42 are coupled to each other through a high-pressure gas tube 46. The second light source 32 and the foot switch 44 are electrically connected to each other through a foot switch cable 44b. The electrical connection between the foot switch 44 and the second light source 32 can be established by wireless. Each of the tubes 45a and 45b is made of a material such as, for instance, silicone, Teflon ®, or other similar materials.

The system controller 5 is operative to perform control of the whole system 1. With the system controller 5, the center display panel 7, the center operation panel 8, and peripheral devices including the electric scalpel device 12, the first light source 22, the second light source 32, the first CCU 23, the second CCU 33, and the gas supply apparatus 41 are communicably connected through communication buses (not shown), respectively.

The monitor 6 has a function of receiving the first and second image signals outputted from the first and second CCUs 23 and 33 to display at least one of the first and second images thereon based on the received first and second image signals.

The center display panel 7 is composed of a display screen, such as a liquid crystal screen or the like. The center display panel 7 allows concentrative display of operating states of the peripheral devices together with the first and second images on the display screen.

The center operation panel 8 is designed to a touch panel and composed of a display section, such as a liquid crystal screen or the like, and a touch-sensitive device integrally formed on the display screen. The display section of the center operation panel 8 has a display function of providing a setting screen on which operable switches (buttons) for the peripheral devices are graphically displayed. The display section has an operating function of operating the operable switches by touching them. The center operation panel 8 is electrically connected to the system controller 5.

Specifically, the operator touches at least one of the operable switches with, for example, a finger so that the touch-sensitive device sets operating conditions corresponding to at least one of the touched operable switches to remotely send to the system controller 5 instructions for operating a corresponding one of the peripheral devices based on the set operating conditions. These remote operations of the graphical operable switches on the center operation panel 8 with respect to the peripheral devices are substantially identical to direct operations of operable switches directly attached to the peripheral devices.

The peripheral devices including the electric scalpel device 12, the first and second light sources 22 and 32, the first and second CCUs 23 and 33, and the gas supply apparatus 41 are mounted on the cart 9. In addition, the system controller 5, the center display panel 7, and the center operation panel 8 are mounted on the cart 9.

Figure 2:
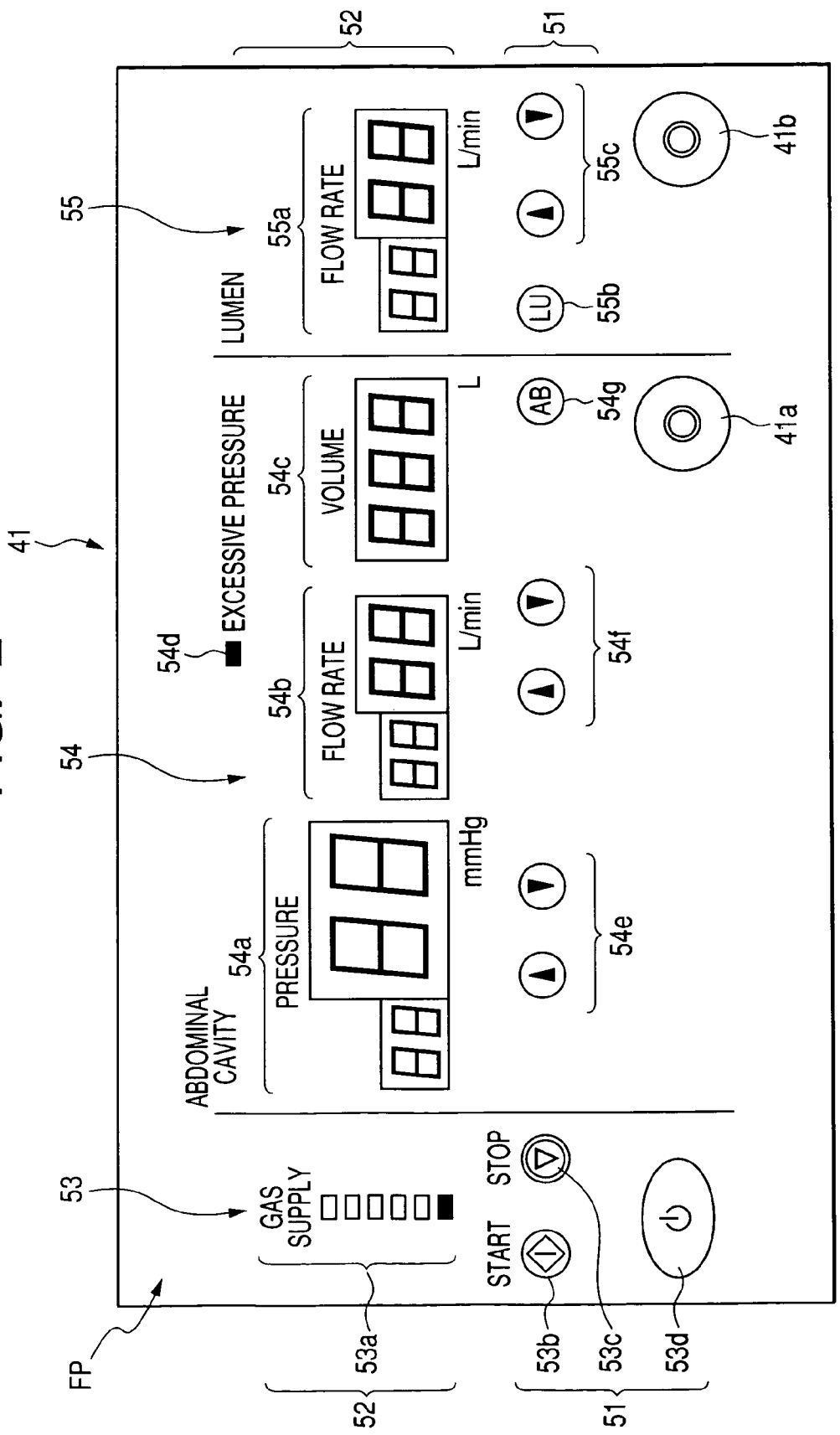
FIG. 2 is a view schematically illustrating a configuration example of a manually operable setting section and a display section provided on a front panel of a gas supply apparatus illustrated in FIG. 1.

On the other hand, as shown in FIG. 2, a front panel FP is attached along one side of a housing of the gas supply apparatus 41; this side is provided with the first and second adapters 41a and 41b.

A manually operable setting section 51 and a display section 52 are graphically displayed on the front panel FP of the gas supply apparatus 41. The manually operable setting section 51 and display section 52 are divided into, for instance, three graphical setting and display sections 53, 54, and 55.

The setting and display section 53 serves as a setting and display section that allows the operator to enter instructions related to the carbon dioxide gas supplied from the $CO_2$ bottle 42. In addition, the $CO_2$ supply-source setting and display section 41C is designed to display the state of carbon dioxide gas supplied from the $CO_2$ bottle 42.

The setting and display section 54 serves as a setting and display section for an abdominal cavity. Specifically, the abdominal-cavity setting and display section 54 allows the operator to set parameters related to the pressure inside the abdominal cavity AC and the carbon-dioxide gas insufflation thereof. The abdominal-cavity setting and display section 54 allows the operator to enter instructions related to the pressure inside the abdominal cavity AC and the carbon-dioxide gas insufflation thereof. The abdominal-cavity setting and display section 54 is designed to display the state of the abdominal cavity AC depending on the carbon dioxide gas being insufflated thereinto.

The setting and display section 55 serves as a setting and display section for lumen BC. Specifically, the lumen setting and display section 55 allows the operator to set parameters related to the carbon-dioxide gas insufflation of the lumen BC; the lumen setting and display section 55 is designed to display the state of the lumen BC depending on the carbon dioxide gas being insufflated thereinto.

The first adaptor 41a is attached to the lower side of the abdominal-cavity setting and display section 54 of the front panel FP; the second adaptor 41b is attached to the lower side of the lumen setting and display section 55 of the front panel FP.

The $CO_2$ supply-source setting and display section 53 is provided with a gas remaining volume indicators 53a as the display section 52. The $CO_2$ supply-source setting and display section 53 is also provided with a gas-supply start button 53b, a gas-supply stop button 53c, and a power switch 71 as the manually operable setting section 51.

The abdominal-cavity setting and display section 54 is provided with abdominal-cavity pressure displays 54a for the pressure inside the abdominal cavity AC, abdominal-cavity flow-rate displays 54b for the abdominal cavity AC, an abdominal-cavity total volume display 54c for the abdominal cavity AC, and an excessive pressure indicator 54d for the abdominal cavity AC as the display section 52.

The abdominal-cavity setting and display section 54 is provided with abdominal-cavity pressure setting buttons 54e for the pressure inside the abdominal cavity AC, abdominal-cavity flow-rate setting buttons 54f for the abdominal cavity AC, and an abdominal-cavity select button 54g (see "AB" in FIG. 2) as the manually operable setting section 51.

The lumen setting and display section 55 is provided with lumen pressure displays 55a for the lumen BC as the display section 52.

The lumen setting and display section 55 is provided with lumen pressure setting buttons 55c for the lumen BC and a lumen select button 55b (see "LU" in FIG. 2) as the manually operable setting section 51.

The power switch 53d serves as a switch that permits the operator to turn power on and off to the apparatus 41. The gas-supply start button 53b is a button that allows the operator to send an instruction to start the supply of the carbon dioxide gas into the abdominal cavity AC to a first controller 67 described hereinafter. The gas-supply stop button 53c is a button that permits the operator to send an instruction to stop the supply of the carbon dioxide gas to the first controller 67.

The pressure setting buttons 54e allow the operator to send instructions to change the corresponding parameter (the pressure inside the abdominal cavity AC) to a pressure setting. The flow-rate setting buttons 54f enable the operator to send instructions to change the corresponding parameter (the flow-rate of the carbon dioxide gas to be delivered into the abdominal cavity AC) to a flow-rate setting. The flow-rate setting buttons 55c permit the operator to send instructions to change the corresponding parameter (the flow-rate of the carbon dioxide gas being delivered into the lumen BC) to a flow-rate setting.

Specifically, the pressure setting buttons 54e include an up button and a down button. Every time the operator clicks the up button, the pressure setting inside the abdominal cavity AC turns up; every time the operator clicks the down button, the pressure setting turns down. The pressure setting variably determined by the up and down buttons 54e is sent to the first controller 67 every time at least one of the up and down buttons 54e is operated.

Similarly, the flow-rate setting buttons 54f include an up button and a down button. The flow-rate setting of the carbon dioxide gas to be insufflated into the abdominal cavity AC turns up every time the operator clicks the up button; the flow-rate setting turns down every time the operator clicks the down button. The flow-rate setting variably set by the up and down buttons 54f is sent to the first controller 67 every time at least one of the up and down buttons 54f is operated.

Furthermore, the flow-rate setting buttons 55c include an up button and a down button. The flow-rate setting of the carbon dioxide gas to be insufflated into the lumen BC turns up every time the operator clicks the up button; the pressure setting turns down every time the operator clicks the down button. The flow-rate setting variably set by the up and down buttons 55c is sent to the first controller 67 every time at least one of the up and down buttons 55c is operated.

The gas remaining volume indicators 53a are vertically arranged so that a top indicator that is lighting indicates the amount of carbon dioxide gas available in the $CO_2$ bottle 42.

The right-side pressure display of the displays 54a is configured to display a pressure value (in mmHg) based on a measured value of a pressure sensor 65 described hereinafter. The left-side pressure display of the displays 54a is configured to display the pressure setting determined based on the operations of, for example, the pressure setting buttons 54e.

The right-side flow-rate display of the displays 54b is configured to display a flow-rate (in L/min) based on a measured value of a first flow-rate sensor 66A described hereinafter. The left-side flow-rate display of the displays 54b is configured to display the flow-rate setting determined based on the operations of, for example, the flow-rate setting buttons 54f.

The total volume display 54c is configured to display a total amount of carbon dioxide gas calculated by the first controller 67 based on the measured value of the first flow-rate sensor 66A.

The excessive pressure indicator 54d consists of, for example, red LED (light emitting diode). The excessive pressure indicator 54d is configured to turn on or flash on and off based on a control signal sent from the first controller 67 at anytime the pressure measured by the pressure sensor 65 exceeds a threshold value of the pressure inside the abdominal cavity AC by a predetermined pressure. The turning-on or the flashing of the excessive pressure indicator 54d allows the operator to visually recognize that the pressure inside the abdominal cavity AC exceeds the threshold value by the predetermined pressure or more.

When the operator turns on the abdominal cavity select button 54g, the button 54g is configured to send to the first controller 67 an instruction to make it execute operations for supplying the carbon dioxide gas into the abdominal cavity AC. In other words, when the operator turns on the abdominal cavity select button 54g, the button 54g is configured to send to the first controller 67 an instruction to change the operation mode thereof to an abdominal cavity insufflation mode.

The right-side flow-rate display 55a is configured to display a flow-rate (in L/min) based on a measured value of a second flow-rate sensor 66B described hereinafter. The left-side flow-rate display of the displays 55a is configured to display the flow-rate setting determined based-on the operations of, for example, the flow-rate setting buttons 55c.

When the operator turns on the lumen select button 55b, the button 55b is configured to send to the first controller 67 an instruction to make it execute operations for supplying the carbon dioxide gas into the lumen BC. In other words, when the operator turns on the lumen select button 55b, the button 55b is configured to send to the first controller 67 an instruction to change the operation mode thereof to a lumen insufflation mode.

Incidentally, an excessive pressure indicator that is the same as the excessive pressure indicator 54d may be provided on the lumen setting and display section 55.

The structures of the manually operable setting section 51 and the display section 52 in the front panel FP allow the operator to easily give instructions to the first controller 67 and to easily visually recognize the parameters related to the abdominal cavity AC and the lumen BC.

Next, a structure of the gas supply apparatus 41 will be described hereinafter with reference to FIG. 3.

Figure 3:
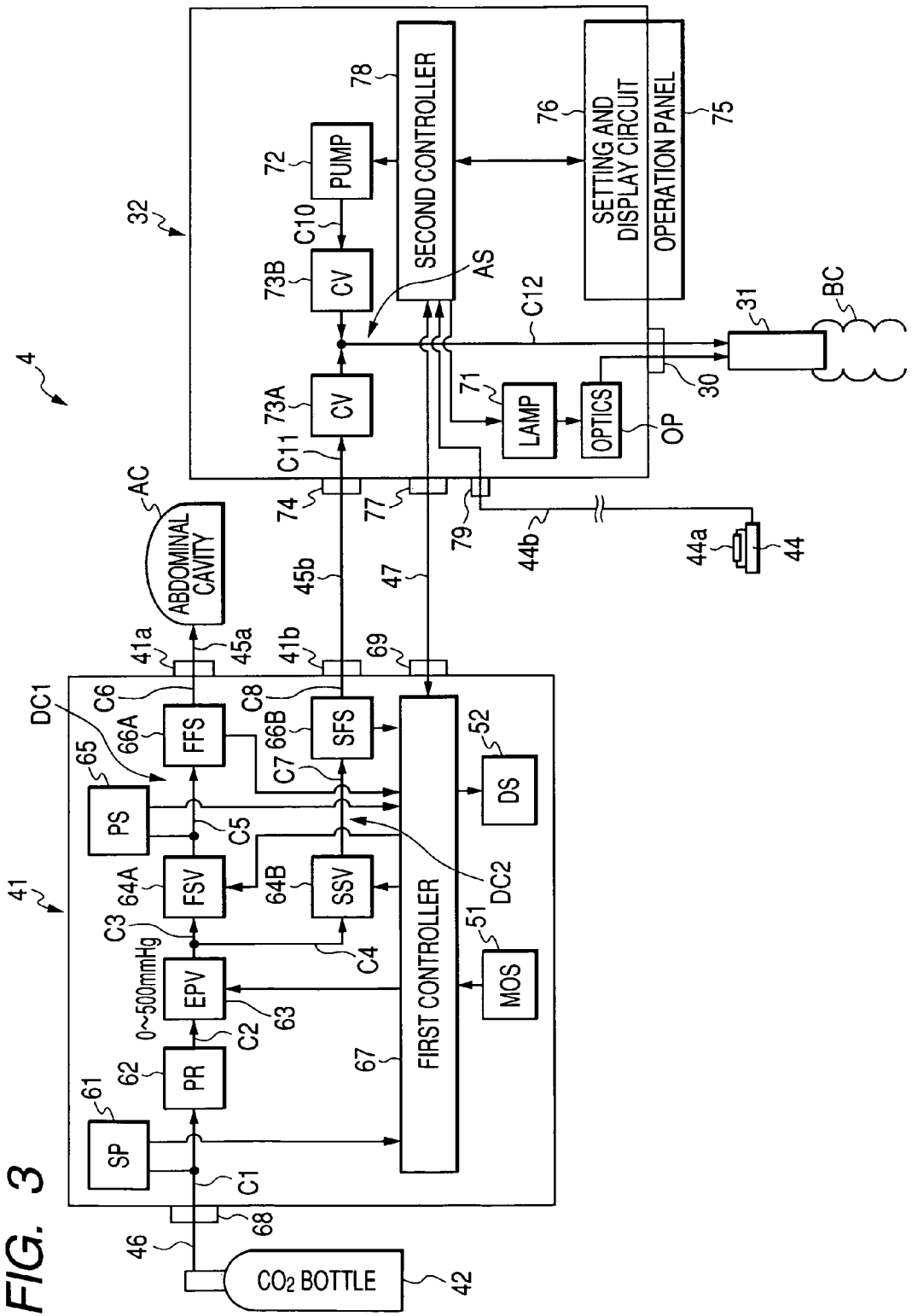
FIG. 3 is a block diagram illustrating a schematic structure of the gas supply system illustrated in FIG. 1.

As shown in FIG. 3, the gas supply apparatus 41 includes a high pressure adapter 68, a first delivery channel C1, a supply pressure sensor (SP) 61, and a pressure reducing unit (PR) 62. The gas supply apparatus 41 includes a second delivery channel C2, an electropneumatic proportional valve (EPV) 63, a third delivery channel C3, and a fourth delivery channel C4.

In addition, the gas supply apparatus 41 includes first and second electromagnetic valves (solenoid valves) 64A and 64B as examples of open/close valves. The first and second solenoid valves are illustrated in FIG. 3 as FSV and SSV, respectively.

The gas supply apparatus 41 includes a fifth delivery channel C5, a sixth delivery channel C6, the pressure sensor (PS) 65, the first flow-rate sensor (FFS) 66A, and the second flow-rate sensor (SFS) 66B. Moreover, the gas supply apparatus 41 includes a seventh delivery channel C7, an eighth delivery channel C8, the first controller 67, the manually operable setting section (MOS) 51, the display section (DS) 52, and the first and second adapters 41a and 41b.

The gas supply apparatus 41 includes a communications connector 69 communicably connected to the first controller 67, and a communication cable 47 whose one end is connected to the connector 69.

Specifically, the $CO_2$ bottle 42 has a discharge port (cock) to which one end of the high-pressure gas tube 46 is joined. The other end of the high-pressure gas tube 46 is joined to the high-pressure adapter 68. The high-pressure adapter 68 is joined to an inlet of the pressure reducing unit 62 via the first delivery channel C1. The supply pressure sensor 61 is attached to the first delivery channel C1. An outlet of the pressure reducing unit 62 is coupled to an inlet of the electropneumatic proportional valve 63 via the second delivery channel C2.

An outlet of the electropneumatic proportional valve 63 is branched into the third delivery channel C3 for the abdominal cavity AC and the fourth delivery channel C4 for the lumen BC.

One branched channel C3 is coupled to an inlet of the first solenoid valve 64A. An outlet of the first solenoid valve 64A is coupled to the fifth delivery channel C5 to which the pressure sensor 65 is attached. The fifth delivery channel C5 is coupled to an inlet of the first flow rate sensor 66A whose outlet is coupled through the sixth delivery channel C6 and the first adapter 41a to the one end of the abdominal cavity tube 45a. The other end of the tube 45a is coupled to the third trocar 16, and the third trocar 16 is inserted into the abdominal cavity AC of the patient 10.

The other branched channel C4 is coupled to an inlet of the second solenoid valve 64B. An outlet of the second solenoid valve 64B is coupled to the seventh delivery channel C7. The seventh delivery channel C7 is coupled to an inlet of the second flow rate sensor 66B whose outlet is coupled through the eighth delivery channel C8 to the second adapter 41b. The second adapter 41b is coupled to the one end of the lumen tube 45b.

In the first embodiment, the third delivery channel C3, the first solenoid valve 64A, the fifth delivery channel C5, the first flow-rate sensor 66A, the sixth delivery channel C6, the first adapter 41a, and the abdominal cavity tube 45a constitute a first $CO_2$ supply path DC 1 directing the carbon dioxide gas into the abdominal cavity AC.

Similarly, the fourth delivery channel C4, the second solenoid valve 64B, the seventh delivery channel C7, the second flow-rate sensor 66B, the eighth delivery channel C8, the second adapter 41b, and the lumen tube 45b constitute part of a second $CO_2$ supply path DC2. The second $CO_2$ supply path DC2 is configured to direct the carbon dioxide gas into the lumen BC.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 62 through the high-pressure gas tube 46, the high pressure adapter 68, and the first delivery channel C1 of the gas supply apparatus 41. The carbon dioxide gas is reduced in pressure by the pressure reducing unit 62 to have a predetermined pressure, and thereafter, guided via the second delivery channel C2 to the electropneumatic proportional valve 63. The electropneumatic proportional valve 63 regulates the pressure of the carbon dioxide gas to a pressure within a range suitable for supply into the inside of the abdominal cavity AC or that of the lumen BC.

More particularly, the electropneumatic proportional valve 63 is provided with a solenoid composed of, for example, a magnet coil (solenoid coil) and a compass needle, which are not shown. The electropneumatic proportional valve 63 is provided with a thin film for pressure control, and a pressure reducing spring. The solenoid is electrically connected to the first controller 67. The electropneumatic proportional valve 63 is configured such that the solenoid controls force applied on the thin film by the pressure reducing spring depending on a control signal applied from the first controller 67, thereby regulating the pressure of the carbon dioxide gas.

Specifically, the electropneumatic proportional valve 63 is designed to change its opening in proportional to a voltage or a current as the control signal applied from the first controller 67 so as to regulate the pressure and the flow-rate of the carbon dioxide gas flowing therethrough within the corresponding appropriate ranges, respectively For example, the electropneumatic proportional valve 63 allows the pressure of the carbon dioxide gas to be regulated within a range from 0 to 500 mmHg based on the control signal applied from the first controller 67.

For example, the range of the pressure of the carbon dioxide gas to be insufflated into the abdominal cavity AC is preferably 0 to 80 mmHg or thereabout; the range of the flow-rate thereof to be insufflated thereinto is preferably 0.1 to 35 L/min or thereabout. Moreover, for example, the range of the pressure of the carbon dioxide gas to be insufflated into the lumen BC is preferably 0 to 500 mmHg or thereabout; the range of the flow-rate thereof to be insufflated thereinto is preferably 1 to 3 L/min or thereabout.

The carbon dioxide gas whose pressure is regulated by the electropneumatic proportional valve 63 is divided into two parts, and they are introduced into the third and fourth delivery channels C3 and C4, respectively. The third and fourth delivery channels C3 and C4 constitute bifurcating cannels, respectively. The divided parts of the carbon dioxide gas are introduced into two supply paths constituting the first $CO_2$ supply path DC1 directing the carbon dioxide gas into the abdominal cavity AC and the second $CO_2$ supply path DC2 directing it into the lumen BC, respectively.

Specifically, the downstream side of the electropneumatic proportional valve 63 is separated into the first $CO_2$ supply path DC1 and the second $CO_2$ supply path DC2 through the third and fourth delivery channels C3 and C4.

The supply pressure sensor 61 is electrically connected to the first controller 67. The supply pressure sensor 61 has a function of detecting the pressure of the carbon dioxide gas flowing from the $CO_2$ bottle 42 to the first delivery channel C1 to send the detected result (detected pressure value) to the first controller 67.

Each of the first and second solenoid valves 64A and 64B is electrically connected to the first controller 67 and configured to open and close based on control signals sent from the first controller 67. The opening and closing of the first solenoid valve 64A allow the first $CO_2$ supply path DC1 to open and close, respectively. Similarly, the opening and closing of the second solenoid valve 64B permit the second $CO_2$ supply path DC2 to open and close, respectively.

The pressure sensor 65 is electrically connected to the first controller 67. The pressure sensor 65 has a function of measuring a pressure in the fifth delivery channel C5, in other words, a pressure inside the abdominal cavity AC, thereby sending the measured result to the first controller 67.

The first and second flow rate sensors 66A and 66B are electrically connected to the first controller 67. The first flow rate sensor 66A has a function of detecting the flow rate of the carbon dioxide gas flowing through the first solenoid valve 64A and the fifth delivery channel C5. Similarly, the second flow rate sensor 66B is operative to detect the flow rate of the carbon dioxide gas flowing through the second solenoid valve 64B and the seventh delivery channel C7. Each of the first and second flow rate sensors 66A and 66B is configured to send the detected result to the first controller 67.

The first controller 67 is operative to receive the measured values outputted from the supply pressure sensor 61, the pressure sensor 65, the first and second flow rate sensors 66A and 66B. The first controller 67 is programmed to execute opening control (pressure control) of the electropneumatic proportional valve 63, opening and closing controls of each of the first and second solenoid valves 64A and 64B, and display control of the display section 52 based on the received measured values.

In addition, the manually operable setting section 51 is electrically connected to the first controller 67. The first controller 67 is also programmed to execute opening control (pressure control) of the electropneumatic proportional valve 63, opening and closing controls of each of the first and second solenoid valves 64A and 64B, and display control of the display section 52 based on the instructions sent from the manually operable setting section 51.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 62 through the high-pressure gas tube 46, the high pressure adapter 68, and the first delivery channel C1 of the gas supply apparatus 41. The carbon dioxide gas is reduced in pressure by the pressure reducing unit 62 to have the predetermined pressure. Thereafter, the carbon dioxide gas is delivered to the electropneumatic proportional valve 63 so that the pressure and flow-rate is regulated based on the control signals sent from the first controller 67.

The carbon dioxide gas with its pressure and flow-rate regulated is selectively switched to either the first $CO_2$ supply path DC1 or the second $CO_2$ supply path DC2. The carbon dioxide gas, which is switched to the first $CO_2$ supply path DC1, is supplied into the abdominal cavity AC therethrough. In contrast, the carbon dioxide gas, which is switched to the second $CO_2$ supply path DC2, is supplied to the inside of the second light source 32 through the second $CO_2$ supply path DC2 extending therein. The carbon dioxide gas supplied into the second light source 32 is delivered through the extending path DC2, the flexiblescope 31, and so on into the lumen BC.

In the first embodiment, the second light source 32 is provided with a light-source lamp, referred to simply as lamp, 71 and an optics OP configured to guide illumination light emitted from the lamp 71; these lamp 71 and optics OP serve as an illumination light source for the inside of the lumen BC.

In addition, the second light source 32 serves as part of the second $CO_2$ supply path DC2 for the lumen BC and as a source of air therefor in addition to the illumination light guiding function.

More particularly, as shown in FIG. 3, the second light source 32 is provided with an air supply pump, referred to simply as pump, 72 serving as a second gas supply source. The second light source 32 is provided with a channel C10 whose one end is coupled to the pump 72, and a check valve (CV) 73B provided in the channel C10 and configured to prevent air from flowing back to the pump 72.

The second light source 32 is provided with a $CO_2$ inlet adapter 74 coupled to the lumen tube 45b, a channel C11 whose one end is coupled to the $CO_2$ inlet adapter 74, and a check valve (CV) 73A provided in the channel C11 and configured to prevent air from flowing back to the inlet adapter 74.

In addition, the second light source 32 is provided with a channel C12 whose one end is communicably coupled to the confluence of the other ends of the channel C10 and C11. The other end of the channel C12 is coupled to the gas delivery channel inside the universal cord 36 through the connector 30 and the light source connector 36a. The adapter 74, the channel C11, the check valve 73A, the channel C12, the connector adapter 30, the light source connector 36a, the universal cord 36, and the flexiblescope 31 constitute part of the second $CO_2$ supply path DC2.

In addition, in the first embodiment, the channel C10, the check valve 72B, the channel C12, the connector adapter 30, the source connector 36a, the universal cord 36, and the flexiblescope 31 constitute an air supply path AS for delivering air supplied from the pump 72 into the lumen BC. The second light source 32 is configured to select one of the carbon dioxide gas supplied from the gas supply apparatus 41 through the second $CO_2$ supply path DC2 and the air supplied from the pump 72 through the air supply path AS to supply the selected one to the flexiblescope 31.

The second light source 32 has an operation panel 75 that allows the operator to set operating conditions of the second light source 32 and that displays the operating states thereof. The second light source 32 has a setting and display circuit 76 that receives the operating conditions set through the operation panel 75 and executes display control of the operation panel 75.

In the first embodiment, the operation panel 75 and the setting and display circuit 76 allow the operator to selectively switch the air supplied from the pump 72 and the carbon dioxide gas supplied from the gas supply apparatus 41 and to set one or more settings including a flow-rate setting of the switched gas (air or carbon dioxide gas). In addition, the operation panel 75 and the setting and display circuit 76 are cooperatively operable to display the settings that the operator can visually recognize.

Furthermore, the second light source 32 has a communications connector 77 to which the other end of the communication cable 47 is connected, and a second controller 78 communicably connected to the connector 77 so that the first controller 67 and the second controller 78 can communicate with each other through the communication cable 47 and the like. The second controller 78 is electrically connected to the pump 72 and operative to control start of air-supply, stop of the air-supply, and air-flow-rate of the pump 72.

The second controller 78 is electrically connected to a controller of the lamp 71 and operative to control the controller of the lamp 71 based on at least one of the settings sent from the setting and display circuit 76.

Based on at least one of settings sent from the setting and display circuit 76, the second controller 78 is operative to select any one of the operation that causes the first controller 67 to supply the carbon dioxide gas to the flexible scope 31 and the operation that causes the pump 72 to supply the air to the flexiblescope 31.

To the second light source 32, a connector 79 is attached. The connector 79 is electrically connected to the second controller 78. The foot switch cable 44b is electrically connected to the connector 79.

Specifically, the second controller 78 is operative to select any one of the operation that causes the first controller 67 to supply the carbon dioxide gas to the flexible scope 31 and the operation that causes the pump 72 to supply the air to the flexiblescope 31 based on the instructions sent from the foot switch 44.

Figure 4:
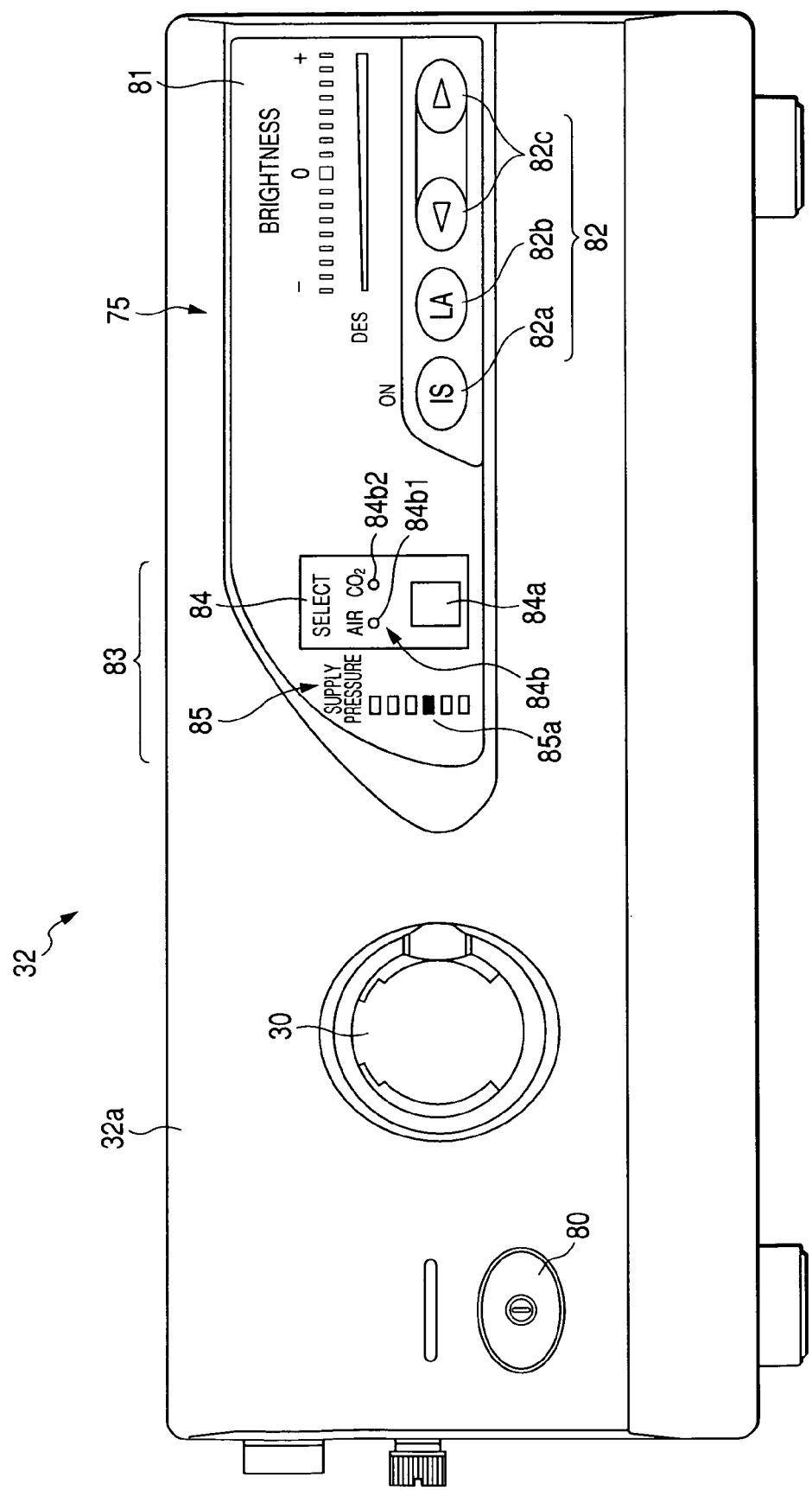
FIG. 4 is a view schematically illustrating a configuration example of a front panel of a second light source illustrated in FIG. 1.

Next, a configuration example of a front panel 32a of the second light source 32 will be described with reference to FIG. 4. As shown in FIG. 4, the connector adapter 30, the operation panel 75, and a power switch 80 are attached to the front panel 32a.

For example, the operation panel 75 is designed to a touch panel integrally formed with a touch-sensitive device.

Specifically, the operation panel 75 has a brightness indicating section 81, a switch section 82, and a lumen insufflation setting section 83.

The brightness indicating section 81 has indicators that are horizontally arranged at regular intervals so that the lighting of any one of the indicators indicates a setting of brightness based on operations of the switch section 82 by the operator.

The switch section 82 includes an insufflation switch 82a, a lamp on/off switch 82b, and brightness control switches 82c.

The insufflation switch 82a is, for example, a graphical toggle switch (on/off switch) with two positions that initiates or halts insufflation by a touch of the operator with, for example, a finger. When the insufflation switch 82a is turned on, an instruction corresponding to the on state of the insufflation switch 82a is sent from the setting and display circuit 76 to the second controller 78 and the insufflation switch 82a lights up. In contrast, when the insufflation switch 82a is turned off, an instruction corresponding to the off state of the insufflation switch 82a is sent from the setting and display circuit 76 to the second controller 78 and the insufflation switch 82a is turned off the light.

The lamp on/off switch 82b is, for example, a graphical toggle switch (on/off switch) with two positions that initiates or halts the lighting of the lamp 71 by a touch of the operator with, for example, a finger. When the lamp on/off switch 82b is turned on, an instruction corresponding to the on state of the lamp on/off switch 82b is sent from the setting and display circuit 76 to the second controller 78 and the lamp on/off switch 82b lights up. In contrast, when the lamp on/off switch 82b is turned off, an instruction corresponding to the off state of the lamp on/off switch 82b is sent from the setting and display circuit 76 to the second controller 78 and the lamp on/off switch 82b is turned off the light.

The brightness control switches 82c include an up button and a down button. Every time the operator clicks the up button, the setting of brightness turns up with the lighting position of one of the indicators 81 turned right. Every time the setting of brightness turns up, the turned-up setting of brightness is sent from the setting and display circuit 76 to the second controller 78 so that the second controller 78 controls the controller of the lamp 72 to adjust the brightness of the light emitted from the lamp 72 based on the setting of brightness.

In addition, every time the operator clicks the down button, the setting of brightness turns down with the lighting position of one of the indicators 81 turned left. Every time the setting of brightness turns down, the turned-down setting of brightness is sent from the setting and display circuit 76 to the second controller 78 so that the second controller 78 controls the controller of the lamp 72 to adjust the brightness of the light emitted from the lamp 72 based on the setting of brightness.

The lumen insufflation setting section 83 includes a supply-source selection switch 84 and a supply pressure indicating section 85.

The supply-source selection switch 84 has a selection switch 84a for selectively switching any one of the carbon dioxide gas supplied from the gas supply apparatus 41 and the air supplied from the pump 72. The supply-source selection switch 84 has supply-source LEDs 84b (84b1 and 84b2) for displaying that any one of the carbon dioxide and the air is selected as the supply-source to the flexiblescope 31. The instruction representing that the selection of any one of the carbon dioxide gas and the air is sent from the setting and display circuit 76 to the second controller 78.

Specifically, the on state of the left side LED 84b1 indicates that the air is selected by the supply-source selection switch 84 as the supply-source to the flexiblescope 31; the on state of the right side LED 84b2 indicates that the carbon dioxide gas is selected by the supply-source selection switch 84 as the supply-source to the flexiblescope 31.

The supply pressure indicating section 85 includes indicators 85a that are vertically arranged. The lighting position of one of the indicators 85a indicates a supply pressure corresponds to the amount of carbon dioxide gas available in the $CO_2$ bottle 42.

The second controller 78 is operative to receive the settings and instructions sent from the setting and display circuit 76 based on the operations on the operation panel 75. The second controller 78 is operative to control at least one of the controller of the lamp 71, the first controller 67 of the gas supply apparatus 41, and the pump 72 based on the received settings and instructions.

While the carbon dioxide gas is supplied through the flexiblescope 31 into the lumen BC based on the control of the first controller 67, the second controller 78 obtains supply-pressure data indicative of a supply-pressure of the carbon dioxide gas from the first controller 67 through the communication cable 47 based on the detected pressure of the pressure sensor 61. The second controller 78 outputs the obtained supply-pressure data to the setting and display circuit 76, and the setting and display circuit 76 turns on one of the indicators 85a, which corresponds to the outputted supply-pressure data.

With the electrical connection between the foot switch 44 and the second controller 78, the depressing operation of the switch portion 44a by the operator allows the instruction to be provided through the foot switch cable 44b to the second controller 78. Incidentally, communications between the foot switch 44 and the second controller 78 can be wirelessly established.

Incidentally, in the first embodiment, for example, a first gas supply unit of the present invention corresponds to the gas supply apparatus 41 except for the first controller 67, the manually operable setting section 51, and the display section 52. In addition, in the first embodiment, for example, a second gas supply unit of the present invention corresponds to the second light source 32 except for the second controller 78, the setting and display circuit 76, and the operation panel 75.

Moreover, in the first embodiment, for example, a selection unit corresponds to the supply-source selection switch 84, and a controller of the present invention corresponds to at least one of the controller 69, the second controller 78, and the setting and display circuit 76.

In the first embodiment, for example, "means for supplying first gas into a body" according to the present invention corresponds to the channel C1, the pressure reducing unit 62, the channel C2, the electropneumatic proportional valve 63, and the second $CO_2$ supply path DC2.

In the first embodiment, for example, "means for supplying second gas into the body" according to the present invention corresponds to the channels C10 and C12, the pump 72, the check valve 73B, and the flexiblescope 31.

In the first embodiment, for example, "means for sending an instruction to select any one of the first gas and the second gas" according to the present invention corresponds to the supply-source selection switch 84.

Figure 5:
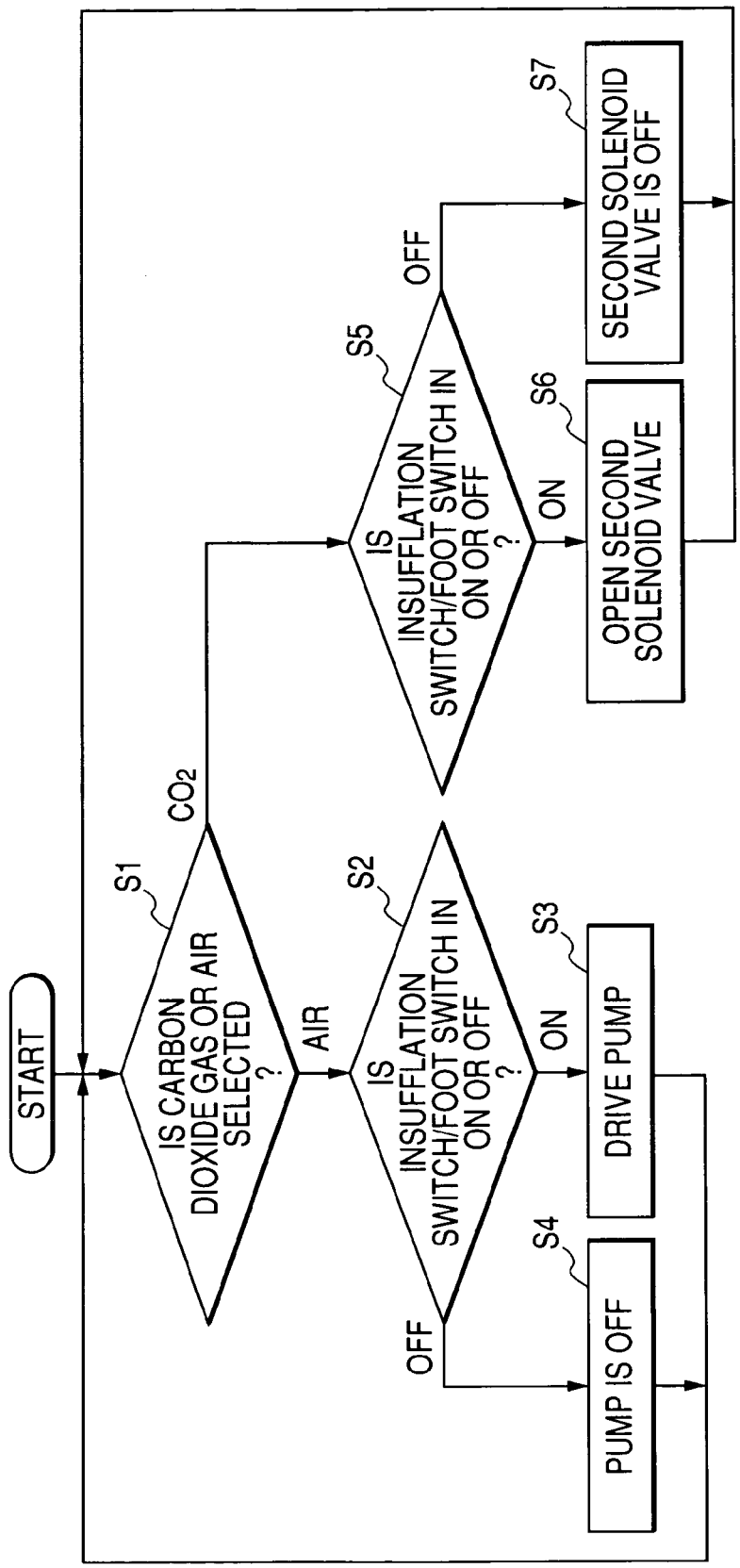
FIG. 5 is a flowchart schematically illustrating an example of operations of a second controller and a first controller illustrated in FIG. 3.

In the first embodiment, for example, "means for selectively insufflating any one of the first gas and second gas into the body" according to the present invention corresponds to the operations of the second controller 78, the first controller 67, and the setting and display circuit 76 illustrated in steps S1 to S7 in FIG. 5.

In the first embodiment, the channels and the like provide airtight junction therebetween provide airtight junction therebetween.

Next, operations of the surgical system 1 with the gas supply system 4 according to the first embodiment will be described hereinafter.

For example, when carrying out laparoscopic surgery employing the surgical system 1, the operator inserts the rigidscope 21 into the inside of the abdominal cavity AC with the flexiblescope 31 being inserted into the lumen BC, such as a large intestine present in the abdominal cavity AC. The operator specifies and treats at least one site to be treated in the abdominal cavity AC and/or the lumen BC.

Specifically, before surgery, the operator or an assistant opens the cock of the $CO_2$ bottle 42. The opening of the cock of the $CO_2$ bottle 42 causes the carbon dioxide gas to flow out of the bottle 42 through the high-pressure gas tube 46, thereby flowing into the gas supply apparatus 41. The gas flowing into the apparatus 41 is introduced through the first delivery channel C1 to the pressure reducing unit 62.

The carbon dioxide gas is reduced in pressure by the pressure reducing unit 62 to have the predetermined pressure, thereby being guided via the second delivery channel C2 to the inlet of the electropneumatic proportional valve 63.

Under a state before surgery, the electropneumatic proportional valve 63 remains closed, which causes the carbon dioxide gas not to flow the downstream thereof. Incidentally, under a state before surgery, each of the first and second solenoid valves 64A and 64B is in off.

When starting surgery, the power switches 53d and 80 are turned on by, for example, the operator. In response to the turning-on of the switch 53d, the right-side pressure display 54a of the front panel FP is ready to display the measured value by the pressure sensor 65, and the foot switch 44 becomes a state that allows the operator to operate it.

In order to insufflate the carbon dioxide gas into the abdominal cavity AC to distend it, the operator turns on each of the abdominal-cavity select button 54g and the gas-supply start button 53b. The instructions corresponding to the turning-on of the buttons 54g and 53b are sent from the manually operable setting section 51 to the first controller 67.

On the left-side pressure display 54a, the pressure setting inside the abdominal cavity AC, which has been previously set on, for example, the center operation panel 8 as a default value, is displayed. Similarly, on the left-side flow-rate display 54b, the flow-rate setting of the carbon dioxide gas to be insufflated into the abdominal cavity AC, which has been previously set on, for example, the center operation panel 8 as a default value, is displayed.

In cases where no pressure setting inside the abdominal cavity AC has been previously determined, the operator appropriately can operate the pressure setting buttons 54e to determine the pressure setting inside the abdominal cavity AC. The instruction corresponding to the pressure setting inside the abdominal cavity AC is sent from the manually operable setting section 51 to the first controller 67. Similarly, in cases where no flow-rate setting for the carbon-dioxide gas insufflation of the abdominal cavity AC has been previously determined, the operator appropriately can operate the flow-rate setting buttons 54f. The instruction corresponding to the flow-rate setting is sent from the manually operable setting section 51 to the first controller 67. The determined pressure setting and flow-rate setting are displayed on the left-side pressure display 54a and the left-side flow-rate display 54b, respectively, based on the operations of the manually operable setting section 51.

Operations of the abdominal cavity select button 54g and the gas-supply start button 53b allow the first controller 67 to start insufflation of the carbon dioxide gas with its pressure regulated suitable for the abdominal cavity AC thereinto.

Specifically, the first controller 67 enters abdominal-cavity insufflation mode based on the turning-on of the abdominal cavity select button 54g. Under the abdominal-cavity insufflation mode, the first controller 67 opens the electropneumatic proportional valve 63 and the first solenoid valve 64A, and controls the opening of the valve 63 so that the pressure and the flow-rate of the carbon dioxide gas flowing therethrough are regulated within the corresponding ranges, respectively.

This results in that the carbon dioxide gas with its pressure and flow-rate regulated, respectively, passes through the first solenoid valve 64A to be guided to both the third delivery channel C3 directing to the abdominal cavity AC and the fourth delivery channel C4 directing to the lumen BC.

Incidentally, in the first embodiment, the range of the pressure of the carbon dioxide gas to be insufflated into the abdominal cavity AC is set to a range of 0 to 80 mmHg or thereabout; the range of the flow-rate thereof to be insufflated thereinto is set to a range of 0.1 to 35 L/min or thereabout.

Because the second solenoid valve 64B is closed, no carbon dioxide gas is supplied through the second solenoid valve 64B. In contrast, because the first solenoid valve 64A is opened, the carbon dioxide gas is supplied into the abdominal cavity AC through the third delivery channel C3, the first solenoid valve 64A, the fifth delivery channel C5, the first flow rate sensor 66A, the abdominal cavity tube 45a, and the third trocar 16. The carbon dioxide gas insufflated into the abdominal cavity AC distends the abdominal cavity AC.

While the carbon dioxide gas is supplied into the abdominal cavity AC, the pressure sensor 65 measures the pressure of the carbon dioxide gas in the fifth delivery channel C5, and the first flow-rate sensor 66A measures the flow rate of the carbon dioxide gas flowing through the fifth delivery channel C5. The pressure sensor 65 and the first flow-rate sensor 66A send the measured results to the first controller 67.

The first controller 67 receives the measured results. The first controller 67 controls the opening of the electropneumatic proportional valve 63 based on the measured results. The control of the opening of the valve 63 causes the pressure and the flow-rate of the carbon dioxide gas into the abdominal cavity AC to be regulated within the corresponding range of, for example, 0 to 80 mmHg or thereabout and that of, for example, 0.1 to 35 L/min thereabout, respectively.

When the pressure inside the abdominal cavity AC of the patient 10 reaches the pressure setting set on the front panel FP, the operator instructs the second controller 78 of the second light source 32 to insufflation into the lumen BC.

At first, the operator checks which supply-source LED has lighted. In the first embodiment, it has been previously determined that any one of the supply-source LEDs 84b1 and 84b2 is initially lighted.

For example, in order to specify the carbon dioxide gas as the supply-source for insufflation of the lumen BC when the supply-source LED 84b1, which corresponds to the air, is lighted, the operator pushes the selection switch 84a at least one time until the supply-source LED 84b2, which corresponds to the carbon dioxide gas, is lighted. Similarly, for specifying the air as the supply-source for insufflation of the lumen BC when the supply-source LED 84b2, which corresponds to the carbon dioxide gas, is lighted, the operator pushes the selection switch 84a at least one time until the supply-source LED 84b1, which corresponds to the air, is lighted. The lighting controls of the LEDs 84b1 and 84b2 are executed by the setting and display circuit 76.

The instruction representing selection of any one of the carbon dioxide gas and the air as the supply-source for insufflation of the lumen BC based on at least one operation of the selection switch 84a is sent from the setting and display circuit 76 to the second controller 78.

On the left-side flow-rate display 55a, the flow-rate setting for the insufflation of the lumen BC with the carbon dioxide gas, which has been previously set on, for example, the center operation panel 8 as a default value, is displayed. In cases where no flow-rate setting for the carbon-dioxide gas insufflation of the lumen BC has been previously determined, the operator appropriately can operate the flow-rate setting buttons 55c. The instruction corresponding to the flow-rate setting is sent from the manually operable setting section 51 to the first controller 67. The determined flow-rate setting is displayed on the left-side flow-rate display 55a based on the operations of the manually operable setting section 51.

The operator operates either the insufflation switch 82a on the operation panel 75 or the switch portion 44a of the foot switch 44, instructing the second controller 78 of the second light source 32 to start gas insufflation of the lumen BC through the flexiblescope 31.

Specifically, the second controller 78 of the second light source 32 receives the instruction based on the operation of the insufflation switch 82a or the switch portion 44a. In response to the instruction, the second controller 78 executes any one of operation to control the first controller 67 to supply the carbon dioxide gas to the flexiblescope 31 and that to control the pump 72 to supply the air to the flexiblescope 31.

The $CO_2$/air insufflation operations of the second controller 78 will be described in reference to a flowchart shown in FIG. 5.

At first, the second controller 78 determines whether the carbon dioxide gas or the air is selected as gas-supply source to the flexiblescope 31 based on the instruction representing that the selection of any one of the carbon dioxide gas and the air sent from the setting and display circuit 76 (FIG. 5; step S1).

When the instruction represents the selection of the air as the gas-supply source, the determination in step S1 is "AIR", the second controller 78 determines whether at least one of the insufflation switch 82a and the switch portion 44a of the foot switch 44 is in on state (step S2).

When both the insufflation switch 82a and the switch portion 44a of the foot switch 44 are in off state, the second controller 78 keeps the pump 72 off (step S4), returning to the operation in step S1.

When at least one of the insufflation switch 82a and the switch portion 44a of the foot switch 44 is in on state, the second controller 78 drives the pump 72 to deliver the air with a predetermined pressure and a predetermined feed rate (step S3). The air fed out from the pump 72, as shown in FIG. 3, passes through the channel C10, the check valve 73B, the channel C12, the universal cord 72, and the like to be supplied to the flexiblescope 31. The air is guided by the flexiblescope 31 to be insufflated into the lumen BC, causing the lumen BC to distend.

The second controller 78 repeatedly executes the operations in step S1 to S3 until at least one of the insufflation switch 82a and the switch portion 44a of the foot switch 44 is turned off. When at least one of the insufflation switch 82a and the switch portion 44a of the foot switch 44 is turned off, the second controller 78 controls the pump 72 to stop the delivery of air (step S4), returning to the operation in step S1.

In contrast, when the instruction represents the selection of the carbon dioxide gas as the gas-supply source, the determination in step S1 is "$CO_2$", the second controller 78 determines whether at least one of the insufflation switch 82a and the switch portion 44a of the foot switch 44 is in on state (step S5).

When both the insufflation switch 82a and the switch portion 44a of the foot switch 44 are in off state, the second controller 78 communicates with the first controller 67 via the communication cable 47 to keep the second solenoid valve 64B of the gas supply apparatus 41 closed (step S7), returning to the operation in step S1.

When at least one of the insufflation switch 82a and the switch portion 44a of the foot switch 44 is in on state, the second controller 78 communicates with the first controller 67 via the communication cable 47 to open the second solenoid valve 64B of the gas supply apparatus 41 (step S6).

The first controller 67 of the gas supply apparatus 41 opens the electropneumatic proportional valve 63 and controls the opening of the valve 63 so that the pressure and the flow-rate of the carbon dioxide gas flowing therethrough are regulated within the corresponding ranges, respectively. This results in that the carbon dioxide gas with its pressure and flow-rate regulated, respectively, is guided to the first $CO_2$ supply path DC1 directing the carbon dioxide gas into the abdominal cavity AC and the second $CO_2$ supply path DC2 directing it into the lumen BC.

Incidentally, in the first embodiment, the range of the pressure of the carbon dioxide gas to be insufflated into the lumen BC is set to a range of 0 to 500 mmHg or thereabout; the range of the flow-rate thereof to be insufflated thereinto is set to a range of 1 to 3 L/min or thereabout.

Because the first solenoid valve 64A is closed in the first $CO_2$ supply path DC 1, no carbon dioxide gas is supplied therethrough.

In contrast, because the second solenoid valve 64B is opened, the carbon dioxide gas is supplied into only the fourth delivery channel C4 of the second $CO_2$ supply path DC2. The carbon dioxide gas passes through the second solenoid valve 64B, the seventh delivery channel C7, the second flow-rate sensor 66B, the eighth delivery channel C8, the lumen adapter 41b, and the lumen tube 45b to enter into the second light source 32 through the inlet adapter 74.

Under such a gas supply state, the measured result of the second flow-rate sensor 66B is sent to the first controller 67. The first controller 67 adjusts the opening of the electropneumatic proportional valve 63 so as to regulate the pressure of the carbon dioxide gas flowing therethrough within the corresponding appropriate range of 0 to 500 mmHg or thereabout set forth above. Simultaneously, the first controller 67 adjusts the opening of the electropneumatic proportional valve 63 so as to regulate the flow-rate of it within the corresponding appropriate range of 1 to 3 L/min or thereabout set forth above.

The carbon dioxide gas entered into the second light source 32, as shown in FIG. 3, passes through the channel C11, the check valve 73A, the channel C12, the universal cord 72, and the like to be supplied to the flexiblescope 31. The carbon dioxide as is guided by the flexiblescope 31 to be insufflated into the lumen BC, causing the lumen BC to distend.

The second controller 78 repeatedly executes the operations in step S1, step S5, and step S6 until at least one of the insufflation switch 82a and the switch portion 44a of the foot switch 44 is turned off. When at least one of the insufflation switch 82a and the switch portion 44a of the foot switch 44 is turned off, the second controller 78 causes the first controller 67 to close the second solenoid valve 64B, stopping the $CO_2$ insufflation through the second $CO_2$ delivery path DC2 (step S7), returning to the operation in step S1.

As described above, in the surgical system 1 with the gas supply system 4 according to the first embodiment, manual switching on the operation panel 75 allows easy selecting of the $CO_2$ insufflation and the air insufflation of the flexiblescope 31 without manual handling on the front panel FP.

Specifically, in the first embodiment, it is possible to turn on and off the selection switch 84a on the operation panel 75 independently of the front pane FP on which various switches and buttons for determining the state of the carbon dioxide gas (see FIG. 2) are provided. This turning on and off of the selection switch 84a permits switching of any one of the carbon dioxide gas and the air to be supplied into the lumen BC.

As a result, the operator can recognize and manipulate the selection switch 84a without misleading the various switches and buttons for determining the state of the carbon dioxide gas. This makes it possible to rapidly easily switch any one of the carbon dioxide gas and the air as the gas-supply source for insufflation of the lumen BC.

In addition, in the first embodiment, the operator visually recognizes the supply-source LEDs 84b on the operation panel 75 independently of the front pane FP on which various displays for displaying the state of the carbon dioxide gas (see FIG. 2). This makes it possible for the operator to easily grasp which of these gases is insufflated into the lumen BC, the carbon dioxide gas or the air. As a result, the operator can identify the gas that is currently set as the gas-supply source for insufflation of the lumen BC easily without misleading the various displays for displaying the state of the carbon dioxide gas.

In the first embodiment, the lumen tube 45b is coupled to the $CO_2$ inlet adapter 74 in the second light source 32 (see FIG. 1), which allows the carbon dioxide gas delivered from the gas supply apparatus 41 to enter into the second light source 32. Specifically, the second light source 32 is configured to selectively switch any one of the carbon dioxide gas delivered from the gas supply apparatus 41 and the air fed from the pump 72, thereby supplying the switched one to the flexiblescope 31.

If the air delivered from the pump 72 is used as the gas-supply source for insufflation of the lumen BC, the second light source will be used with the lumen tube 45b removed from the $CO_2$ inlet adapter 74. In this case where the lumen tube 45b removed from the $CO_2$ inlet adapter 74, it will be preferable to close that path in the second light source 32 to prevent air leak, which is communicated with the exterior thereof through the channel C10, the channel C11, and the $CO_2$ inlet adapter 74 from the pump 72.

Figure 6:
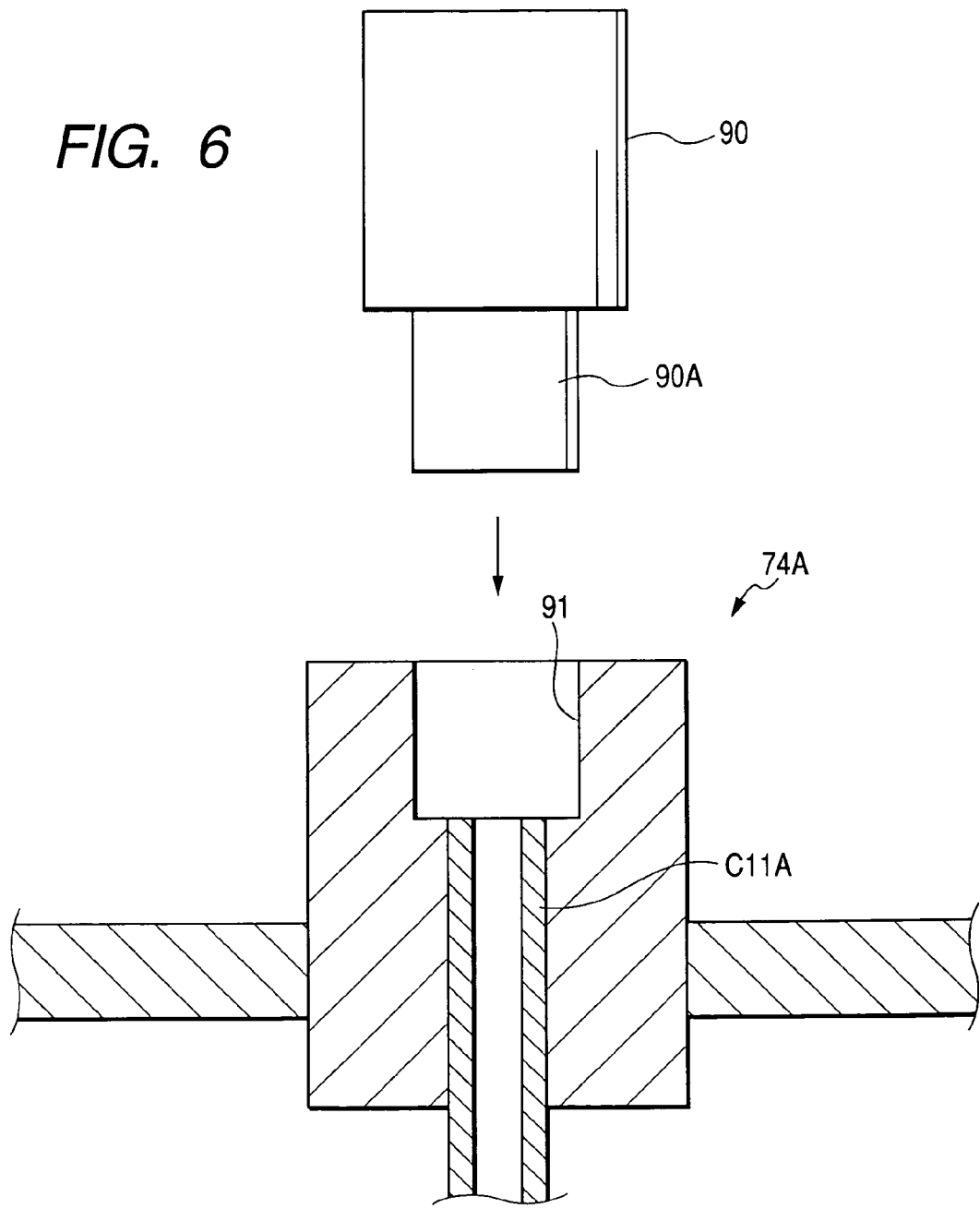
FIG. 6 is an enlarged and partially sectional view of a modification of part of the $CO_2$ inlet adapter illustrated in FIG. 1.

A configuration of a $CO_2$ inlet adapter 74A that is configured to prevent air leak is illustrated in FIG. 6. As illustrated in FIG. 6, the $CO_2$ inlet adapter 74A is attached to one end of a pipe C11A constituting the delivery channel C11, and is formed at its center head portion with a groove 91. The groove 91 allows an end portion of the lumen tube 45b to be fit. The inlet adapter 74A has a cap 90 with one end portion 90A that is airtightly fittable in the groove 91. The cap 90 is mounted on the head portion of the adapter 74A so that the end portion 90A is airtightly fit in the groove 91 to close the pipe C11A airtightly.

When the air is delivered from the pump 72 toward the lumen BC with the lumen tube 45b removed from the $CO_2$ inlet adapter 74A, the configuration of the $CO_2$ inlet adapter 74A prevents part of the delivered air from externally leaking out of the adapter 74A through the pipe C11A. This makes it possible to supply the air delivered from the pump 72 into the lumen BC stably.

Figure 7:
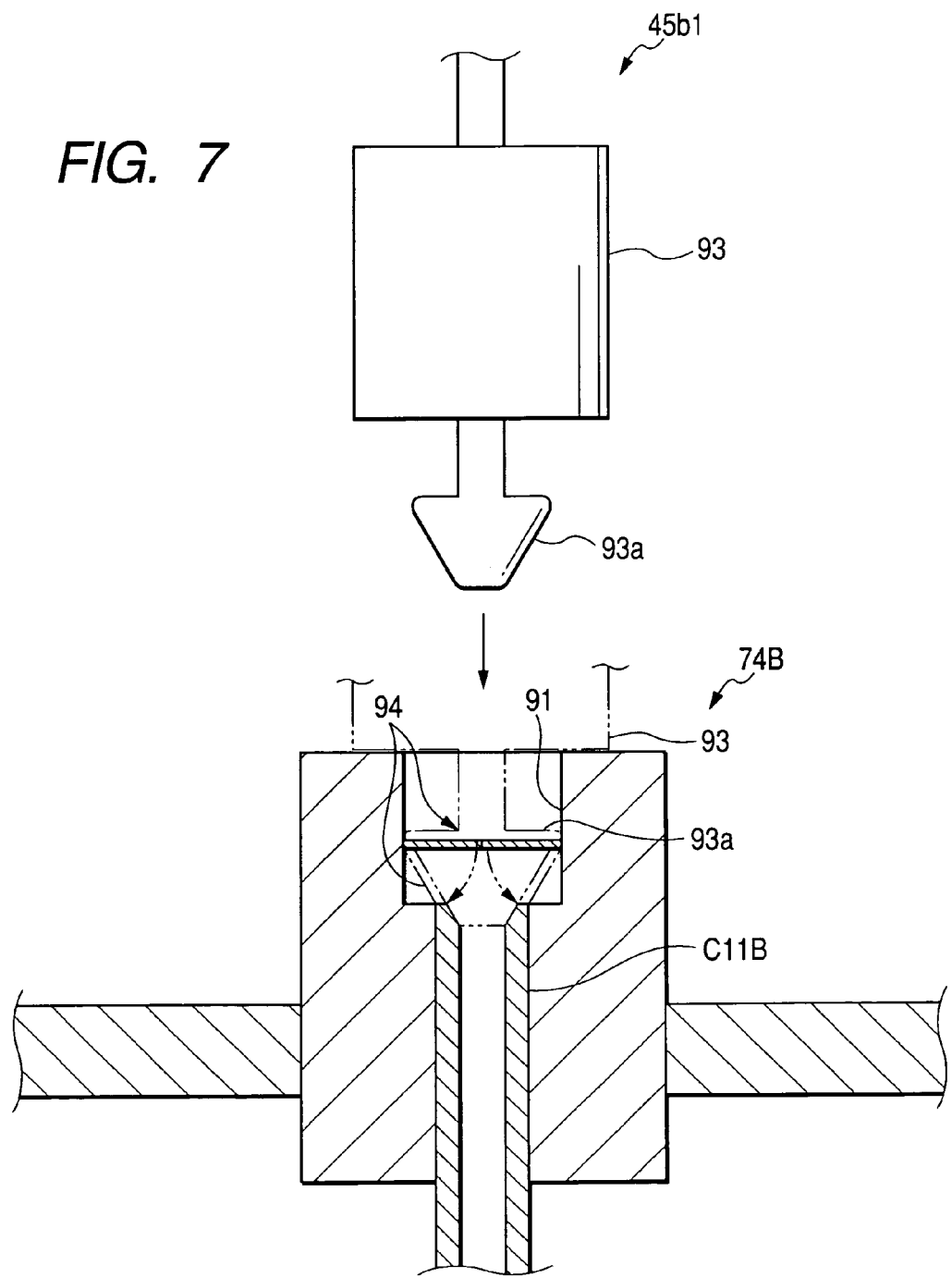
FIG. 7 is a partially enlarged and sectional view of another modification of part of the $CO_2$ inlet adapter illustrated in FIG. 1 and a modification of part of the lumen tube illustrated in FIG. 1.

Another configuration of a $CO_2$ inlet adapter 74B and a lumen tube 45b1 that are configured to prevent air leak is illustrated in FIG. 7. As illustrated in FIG. 7, the lumen tube 45b1 is provided with a connector portion 93 at its one end to be coupled to the $CO_2$ inlet adapter 74B. The connector portion 93 is provided with a fittable end portion 93a at its tip end of the connector portion 93. The end portion 93a is designed to be fittable in one opening end of a pipe C11B and communicable therewith. The pipe C11B constitutes the delivery channel C11.

The $CO_2$ inlet adapter 74B is attached to the one end of the pipe C11B, and is formed at its center head portion with a groove 91. The groove 91 allows the end portion 93a of the lumen tube 45b1 to be accepted.

The inlet adapter 74B has valves 94. The valves 94 are configured to be closed without the end portion 93a of the connector 93 inserted in the groove 91. When the end portion 93a of the connector 93 is inserted into the groove 91, the valves 94 are configured to be pushed open by the end portion 93a. The opening of each valve 94 allows the lumen tube 45b1 to be communicated with the pipe C11B when the end portion 93a of the lumen tube 45b1 is fit in the opening end portion of the pipe C11B.

When the air is delivered from the pump 72 toward the lumen BC with the lumen tube 45b1 removed from the $CO_2$ inlet adapter 74A, because the valves 94 close the pipe 11B, it is possible to prevent part of the delivered air from externally leaking out of the adapter 74A through the pipe C11B. This makes it possible to supply the air delivered from the pump 72 into the lumen BC stably.

Incidentally, the second light source 32 can use the lumen tube 45b with it connected to the $CO_2$ inlet adapter 45b when without using the carbon dioxide gas as a gas for insufflation of the lumen BC.

Figure 8:
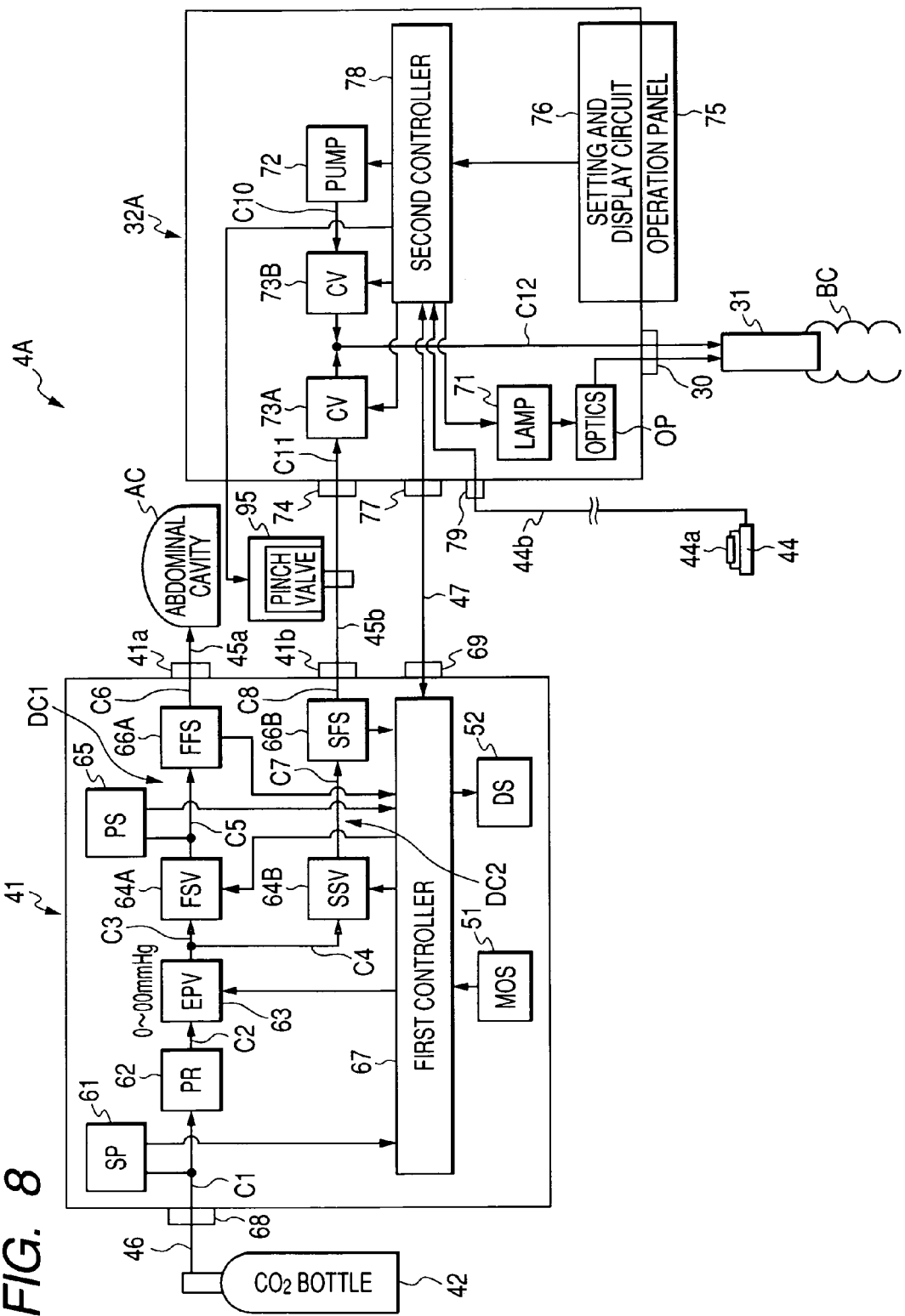
FIG. 8 is a block diagram illustrating a schematic structure of a modification of the gas supply system according the first embodiment.

The configuration of a second light source 32A of a gas supply system 4A according to a modification of the first embodiment is illustrated in FIG. 8. In FIG. 8, the second light source 32A is provided with a pinch valve 95 provided in the lumen tube 45b and electrically connected to the second controller 78 so that the second controller 78 controls the pinch valve 95 open and close.

Specifically, when the air is selected by the supply-source selection switch 84, the second controller 78 outputs a close-control signal to the pinch valve 95 to close it. The pinch valve 95 presses the lumen tube 45b to close the second $CO_2$ supply path DC2 based on the close-control signal.

In contrast, when the carbon dioxide gas is selected by the supply-source selection switch 84, the second controller 78 outputs an open-control signal to the pinch valve 95 to open it. The pinch valve 95 keeps the lumen tube 45b unpressed to keep the second $CO_2$ supply path DC2 open based on the close-control signal.

The configuration of the gas supply system 4A makes it possible to prevent the carbon dioxide gas from flowing into the second light source 32 from the gas supply apparatus 41 when the air is selected by the supply-source selection switch 84, in other words, the air is selected as the gas-supply source for insufflation of the lumen BC.

Figure 9:
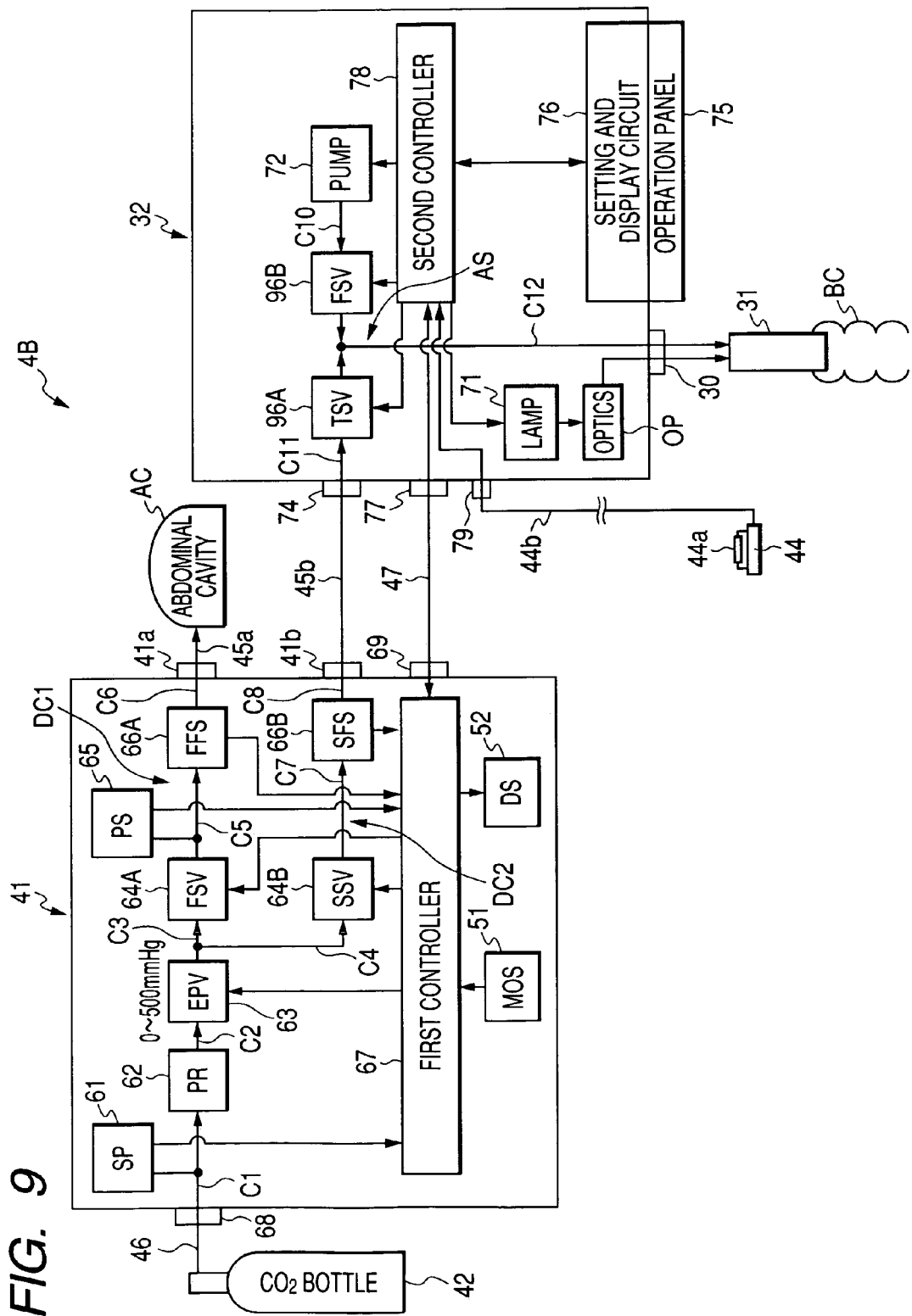
FIG. 9 is a block diagram illustrating a schematic structure of another modification of the gas supply system according to the first embodiment.

The configuration of a second light source 32B of a gas supply system 4B according to another modification of the first embodiment is illustrated in FIG. 9. As illustrated in FIG. 9, the second light source 32B is provided with a third solenoid valve (TSV) 96A in place of the check valve 73A. The third solenoid valve 96A is provided in the channel C11 whose one end is coupled to the $CO_2$ inlet adapter 74 through the channel C11. The third solenoid valve 96A is electrically connected to the second controller 78. Similarly, as illustrated in FIG. 9, the second light source 32B is provided with a fourth solenoid valve (FSV) 96B in place of the check valve 73B. The fourth solenoid valve 96B is provided in the channel C11 whose one end is coupled to the pump 72 through the channel C10. The fourth solenoid valve 96B is electrically connected to the second controller 78.

The third and fourth solenoid valves 96A and 96B are configured to open or close individually based on control signals sent from the second controller 78.

Specifically, when insufflating the carbon dioxide gas supplied from the gas supply apparatus 41 through the second light source 32B, the second controller 78 of the second light source 32B outputs an open-control signal to the third solenoid valve 96A to open it, and outputs a close-control signal to the fourth solenoid valve 96B to close it.

In contrast, when insufflating the air delivered from the pump 72, the second controller 78 of the second light source 32B outputs the open-control signal to the fourth solenoid valve 96B to open it, and outputs the close-control signal to the third solenoid valve 96B to close it.

When no carbon dioxide gas and air is insufflated through the second light source 32B, each of the third and fourth solenoid valves 96A and 96B is in close state, making it possible to keep both the channel C10 and the channel C11 close.

In the configuration of the gas supply system 4B, when the air is selected by the supply-source selection switch 84, the second controller 78 outputs the open-control signal to the third solenoid valve 96A to close it, thereby closing the channel C11 at the downstream of the third solenoid valve 96A.

The configuration of the gas supply system 4B makes it possible to prevent the carbon dioxide gas from flowing through the downstream of the third solenoid valve 96A in the channel C11.

Incidentally, in the first embodiment, the gas supply apparatus 41 is configured to supply the carbon dioxide gas as a predetermined gas, but the gas supply apparatus according to the present invention can be configured to supply inactive gas, such as helium gas as the predetermined gas.

Second Embodiment

A second light source 32C in a gas supply system 4C according to a second embodiment of the present invention has a function of regulating the flow rate of a gas supplied from the second light source 32C, in addition to the function of selectively supplying the carbon dioxide gas and the air into the lumen BC. Incidentally, elements of the gas supply system 4C are substantially identical to those of the gas supply system 4 according to the first embodiment described above. Hence, the same reference characters of the elements of the gas supply system 4 (see FIG. 3) are assigned to the corresponding elements of the gas supply system 4C according to the second embodiment, and therefore, descriptions thereabout are omitted or simplified.

Figure 10:
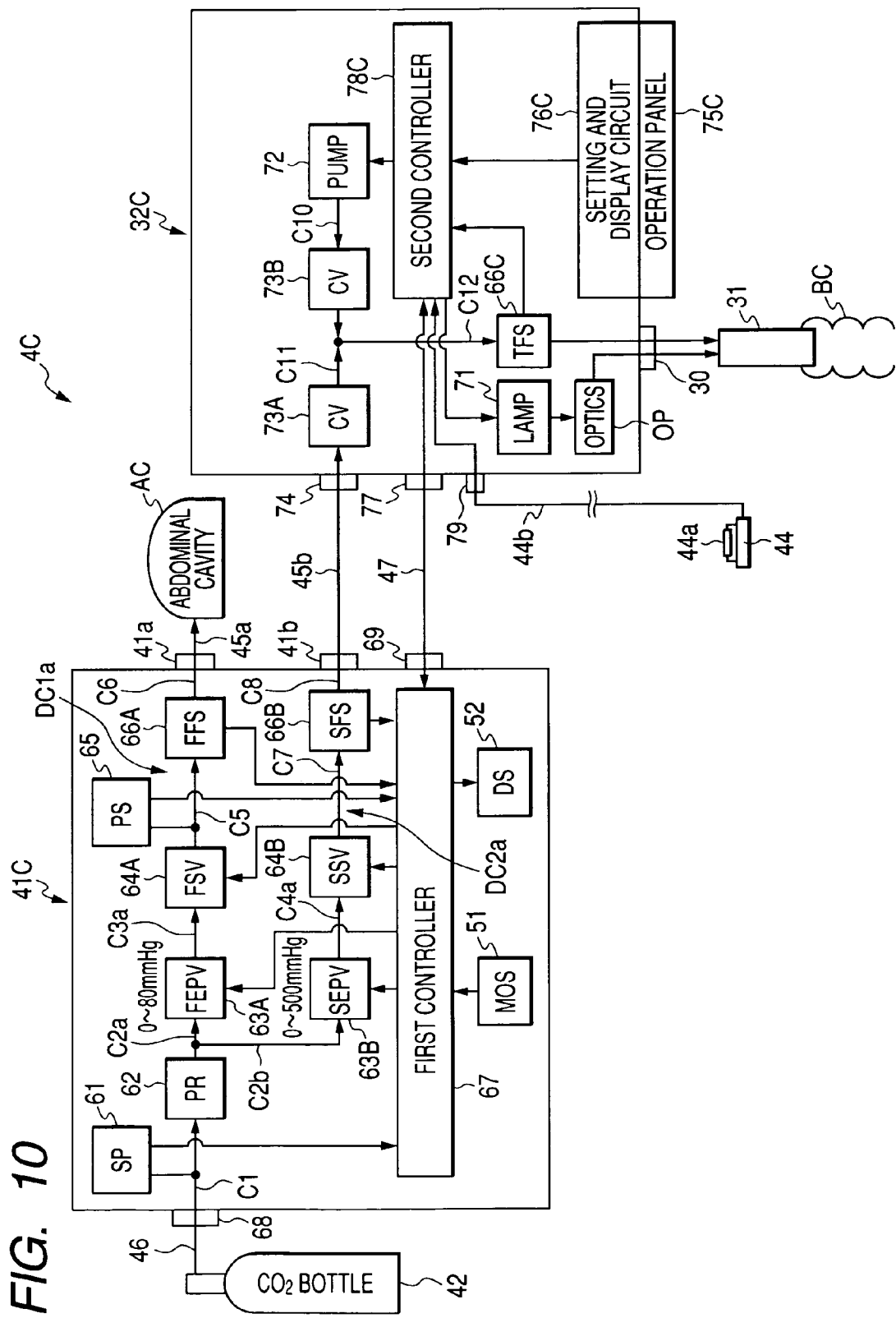
FIG. 10 is a block diagram illustrating a schematic structure of a gas supply system according to a second embodiment of the present invention.

As shown in FIG. 10, the gas supply system 4C is provided with a gas supply apparatus 41C and a second light source 32C.

The gas supply apparatus 41C is provided with channels C2a and C2b into which the downstream of the reducing unit 62 is branched. The gas supply apparatus 41C is provided with first and second electropneumatic proportional valves (FEPV and SEPV) 63A and 63B provided in the branched channels C2a and C2b, respectively. The output side of the first electropneumatic proportional valve 63A is connected to the first solenoid valve 64A through a channel C3a, and that of the second electropneumatic proportional valve 63B is connected to the second solenoid valve 64B through a channel C4a.

Specifically, in the second embodiment, the channel C2a, the first electropneumatic proportional valve 63A, the channel C3a, the first solenoid valve 64A, the fifth channel C5, the first flow-rate sensor 66A, the sixth channel C6, the first adapter 41a, and the abdominal tube 45a constitute a first $CO_2$ supply path DC1a. The first $CO_2$ supply path DC1a works to feed the carbon dioxide gas supplied from the $CO_2$ bottle 42 into the abdominal cavity AC.

Similarly, in the second embodiment, the channel C2b, the second electropneumatic proportional valve 63B, the channel C4a, the second solenoid valve 64B, the seventh channel C7, the second flow-rate sensor 66B, the eighth channel C8, the second adapter 41b, and the lumen tube 45b partly constitute a second $CO_2$ supply path DC2a. The second $CO_2$ supply path DC2a works to feed the carbon dioxide gas supplied from the $CO_2$ bottle 42 into the lumen BC.

The first electropneumatic proportional valve 63A is operative to adjust the pressure of the carbon dioxide gas, which is reduced by the pressure reducing unit 62, within a range of 0 to 80 mmHg or thereabout based on a control signal supplied from the first controller 67. The second electropneumatic proportional valve 63B is operative to adjust the pressure of the carbon dioxide gas, which is reduced by the pressure reducing unit 62, within a range of 0 to 300 mmHg or thereabout based on a control signal supplied from the first controller 67.

The first controller 67 of the gas supply apparatus 41C receives the measured results supplied from the pressure sensor 65 and the first flow-rate sensor 66A. The first controller 67 controls the opening of the first electropneumatic proportional valve 63A based on the measured results. The control of the opening of the valve 63A causes the pressure and the flow-rate of the carbon dioxide gas into the abdominal cavity AC to be regulated within the corresponding range of, for example, 0 to 80 mmHg or thereabout and that of, for example, 0.1 to 35 L/min thereabout, respectively.

In addition, the first controller 67 of the gas supply apparatus 41C receives the measured result supplied from the second flow-rate sensor 66B. The first controller 67 controls the opening of the second electropneumatic proportional valve 63B based on the measured result. The control of the opening of the valve 63B causes the pressure and the flow-rate of the carbon dioxide gas into the lumen BC to be regulated within the corresponding range of, for example, 0 to 300 mmHg or thereabout and that of, for example, 1 to 3 L/min thereabout, respectively.

Because other elements of the gas supply apparatus 41C according to the second embodiment are substantially identical with those of the gas supply apparatus 41 according to the first embodiment, descriptions about the other elements are omitted or simplified.

The second light source 32C is provided with a third flow-rate sensor 66C in addition to the structure of the second light source 32 described in the first embodiment. The third flow-rate sensor 66C is provided in the channel C12 and electrically connected to a second controller 78C. The third flow-rate sensor 66C is operative to measure the flow rate of the carbon dioxide gas flowing through the channel C12.

The second controller 78C of the second light source 32C according to the second embodiment receives the measured result supplied from the third flow-rate sensor 66C. The second controller 78C causes the first controller 67 to control the opening of the second electropneumatic proportional valve 63B based on the measured result. The control of the opening of the valve 63B causes the pressure and the flow-rate of the carbon dioxide gas into the lumen BC to be regulated within the corresponding range of, for example, 0 to 300 mmHg or thereabout and that of, for example, 1 to 3 L/min thereabout, respectively.

Figure 11:
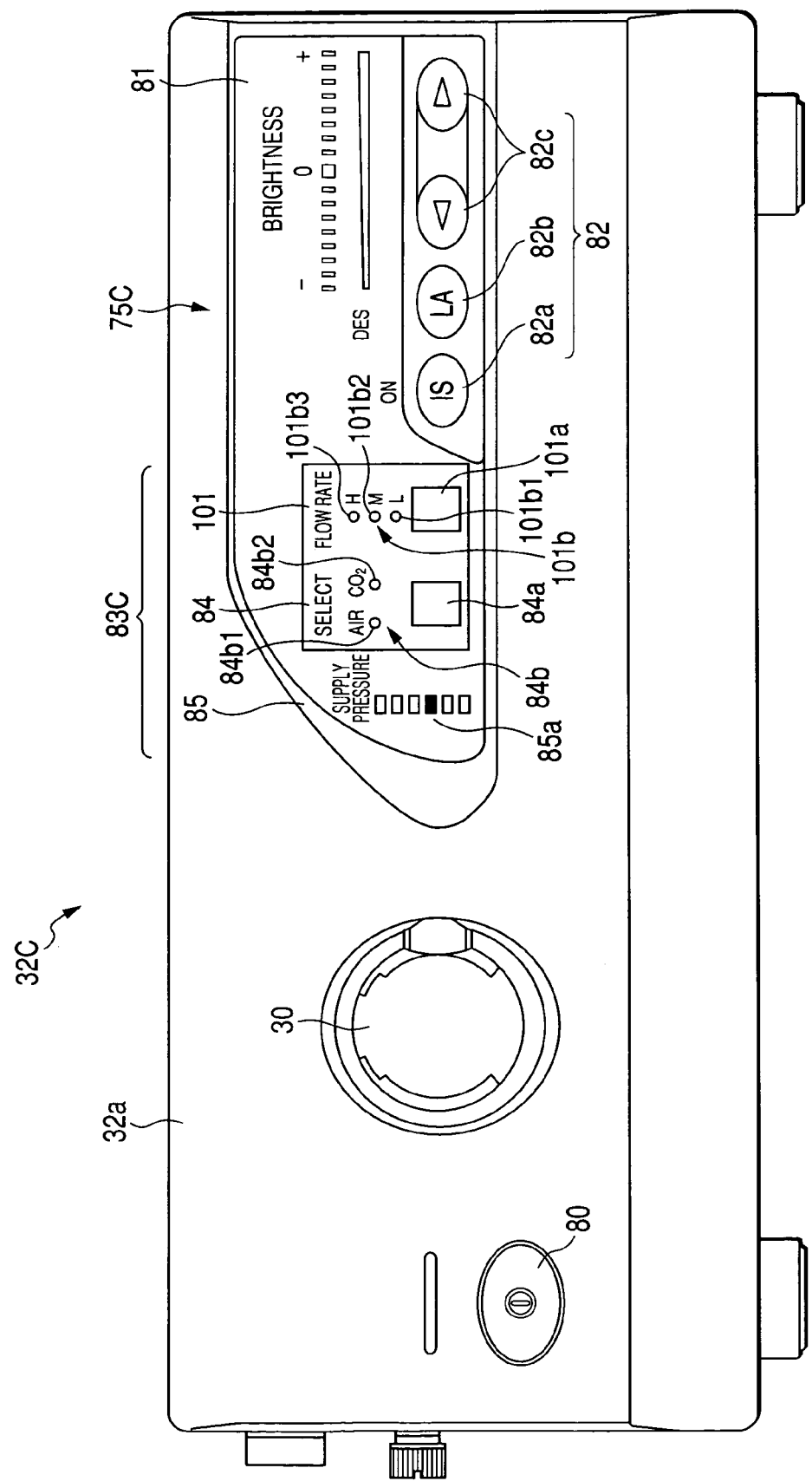
FIG. 11 is a view schematically illustrating a configuration example of a front panel of a second light source illustrated in FIG. 10.

In addition, the second light source 32C according to the second embodiment has an operation panel 75C that allows the operator to set the flow-rate of insufflation gas, such as the carbon dioxide gas or the air, being delivered into the lumen BC to a flow-rate setting. Hence, in addition to the insufflation-gas selection operations (see steps S1 to S7) set forth above, the second light source 32C is operative to control the flow-rate of the selected insufflation gas, Specifically, as illustrated in FIG. 11, to the front panel 32a, an operation panel 75C is attached.

The operation panel 75C includes a lumen insufflation setting section 83C composed of the supply-source selection switch 84, the supply pressure indicating section 85, which has already been described in the first embodiment, and a flow-rate setting and indicating section 101.

The flow-rate setting and indicating section 101 has a selection switch 101a for selectively setting the flow-rate of the insufflation gas into the flexiblescope 31 to any one range in, for example, three different ranges of a High (H) range, a Middle (M) range, and a Low (L) range. The High range of the flow-rate is higher than the Middle range thereof, and the Middle range of the flow-rate is higher than the Low range thereof.

The flow-rate setting and indicating section 101 also has flow-rate indicating LEDs 101b for indicating that any one of the High range, the Middle range, and the Low range is selected by the selection switch 101a.

The flow-rate indicating LEDs 101b include a Low LED 101b1 that is turned on when the Low range is selected by the selection switch 101a, and a Middle LED 101b2 that is turned on when the Middle range is selected by the selection switch 101a. In addition, the flow-rate indicating LEDs 101b include a High LED 101b3 that is turned on when the High range is selected by the selection switch 101a.

The selection switch 101a is, for example, a graphical push switch. Every the selection switch 101a is touched by, for example, the operator, the setting and display circuit 76C toggles to sequentially turn one of the Low LED 101b1, the Middle LED 101b2, and the High LED 101b3 on. In response to the turning on of one of the LEDs 101b1 to 101b3, the setting and display circuit 76C sends, to the second controller 78C, setting information including one of the Low range, the Middle range, and the High range, which corresponds to one of the LEDs 101b1, 101b2, and 101b3 being lighted. In the second embodiment, for example, the Low range represents the range of a flow-rate setting of 1 L/min or thereabout, the Middle range represents the range of a flow-rate setting of 2 L/min or thereabout, and the High range represents the range of a flow-rate setting of 3 L/min.

The second controller 78C is operative to receive the setting information sent from the setting and display circuit 76C. Based on the received setting information, the second controller 78C is operative to control the first controller 67 of the gas supply apparatus 41C and/or the pump 72 to adjust the flow-rate of the insufflation gas selected by the second light source 32C (supply-source selection switch 84) to the flow-rate setting included in the setting information. Because other elements of the second light source 32C according to the second embodiment are substantially identical with those of the second light source 32 according to the first embodiment, descriptions about the other elements are omitted or simplified.

Next, operations of the surgical system 1 with the gas supply system 4C according to the second embodiment will be described hereinafter.

For example, when carrying out laparoscopic surgery employing the surgical system 1, the operator inserts the rigidscope 21 into the inside of the abdominal cavity AC with the flexiblescope 31 being inserted into the lumen BC, such as a large intestine present in the abdominal cavity AC. The operator specifies and treats at least one site to be treated in the abdominal cavity AC and/or the lumen BC.

Incidentally, as the first embodiment, the carbon dioxide gas supplied from the $CO_2$ bottle 42 and introduced to the pressure reducing unit 62 is reduced in pressure by the pressure reducing unit 62 to have the predetermined pressure. The pressure-reduced carbon dioxide gas is branched via the branched channels C2a and C2b to be guided to each inlet of each of the electropneumatic proportional valves 63A and 63B.

Under a state before surgery, each of the electropneumatic proportional valves 63A and 63B remains closed, which causes the carbon dioxide gas not to flow the downstream thereof. Incidentally, under a state before surgery, each of the first and second solenoid valves 64A and 64B is in off.

When starting surgery, the power switches 53d and 80 are turned on by, for example, the operator. In response to the turning-on of the switch 53d, the right-side pressure display 54a of the front panel FP is ready to display the measured value by the pressure sensor 65, and the foot switch 44 becomes a state that allows the operator to operate it.

In order to insufflate the carbon dioxide gas into the abdominal cavity AC to distend it, the operator turns on each of the abdominal-cavity select button 54g and the gas-supply start button 53b. The instructions corresponding to the turning-on of the buttons 54g and 53b are sent from the manually operable setting section 51 to the first controller 67.

In the gas supply apparatus 41C, on the left-side pressure display 54a, the pressure setting inside the abdominal cavity AC, which has been previously set on, for example, the center operation panel 8 as a default value, is displayed. Similarly, on the left-side flow-rate display 54b, the flow-rate setting of the carbon dioxide gas to be insufflated into the abdominal cavity AC, which has been previously set on, for example, the center operation panel 8 as a default value, is displayed.

In cases where no pressure setting inside the abdominal cavity AC has been previously determined, the operator appropriately can operate the pressure setting buttons 54e to determine the pressure setting inside the abdominal cavity AC. The instruction corresponding to the pressure setting inside the abdominal cavity AC is sent from the manually operable setting section 51 to the first controller 67. Similarly, in cases where no flow-rate setting for the carbon-dioxide gas insufflation of the abdominal cavity AC has been previously determined, the operator appropriately can operate the flow-rate setting buttons 54f. The instruction corresponding to the flow-rate setting is sent from the manually operable setting section 51 to the first controller 67. The determined pressure setting and flow-rate setting are displayed on the left-side pressure display 54a and the left-side flow-rate display 54b, respectively, based on the operations of the manually operable setting section 51.

Operations of the abdominal cavity select button 54g and the gas-supply start button 53b allow the first controller 67 to start insufflation of the carbon dioxide gas with its pressure regulated suitable for the abdominal cavity AC thereinto.

Specifically, the first controller 67 enters abdominal-cavity insufflation mode based on the turning-on of the abdominal cavity select button 54g. Under the abdominal-cavity insufflation mode, the first controller 67 opens the first electropneumatic proportional valve 63A and the first solenoid valve 64A, and controls the opening of the valve 63A so that the pressure and the flow-rate of the carbon dioxide gas flowing therethrough are regulated within the corresponding ranges, respectively.

Because the second solenoid valve 64B is closed, no carbon dioxide gas is supplied through the second solenoid valve 64B. In contrast, because the first solenoid valve 64A is opened, the carbon dioxide gas is supplied into the abdominal cavity AC through the third delivery channel C3, the first solenoid valve 64A, the fifth delivery channel C5, the first flow rate sensor 66A, the abdominal cavity tube 45a, and the third trocar 16. The carbon dioxide gas insufflated into the abdominal cavity AC distends the abdominal cavity AC.

While the carbon dioxide gas is supplied into the abdominal cavity AC, the pressure sensor 65 measures the pressure of the carbon dioxide gas flowing through the fifth delivery channel C5, and the first flow-rate sensor 66A measures the flow rate of the carbon dioxide gas flowing through the fifth delivery channel C5. The pressure sensor 65 and the first flow-rate sensor 66A send the measured results to the first controller 67.

The first controller 67 receives the measured results. The first controller 67 controls the opening of the first electropneumatic proportional valve 63A based on the measured results. The control of the opening of the valve 63A causes the pressure and the flow-rate of the carbon dioxide gas into the abdominal cavity AC to be regulated within the corresponding range of, for example, 0 to 80 mmHg or thereabout and that of, for example, 0.1 to 35 L/min thereabout, respectively.

When the pressure inside the abdominal cavity AC of the patient 10 reaches the pressure setting set on the front panel FP, the operator instructs the second controller 78C of the second light source 32C to insufflation of the lumen BC.

At that time, in the operation panel 75C of the second light source 32C, one of the supply sources for insufflation of the lumen BC, which has been previously determined (selected), is indicated by the lighting of the corresponding one of the supply-source LEDs 84b1 and 84b2. For example, when the air has been determined as the supply source for insufflation of the lumen BC, the LED 84b1 is lighted, but when the carbon dioxide gas has been determined as the supply source therefor, the LED 84b2 is lighted.

In addition, in the operation panel 75C of the second light source 32C, one of the flow-rate settings for insufflation of the lumen BC, which has been previously determined (selected), is indicated by the lighting of the corresponding one of the LEDs 101b1 to 101b3. For example, when the flow-rate setting corresponding to the Low range has been determined, the LED 101b1 is lighted, but when the flow-rate setting corresponding to the Middle range has been determined, the LED 101b2 is lighted. Moreover, when the flow-rate setting corresponding to the High range has been determined, the LED 101b3 is lighted.

In cases where the supply source and the flow-rate setting have not been determined yet, the operator appropriately can operate the selection switch 84a of the supply-source selection switch 84 and the selection switch 101a of the flow-rate setting and indicating section 101 to determine the supply source for insufflation of the lumen BC and the flow-rate setting, respectively.

Subsequently, the operator operates either the insufflation switch 82a on the operation panel 75 or the switch portion 44a of the foot switch 44, instructing the second controller 78C of the second light source 32C to start gas insufflation of the lumen BC through the flexiblescope 31.

Specifically, the second controller 78C of the second light source 32C receives the instruction based on the operation of the insufflation switch 82a or the switch portion 44a. In response to the instruction, the second controller 78C executes any one of operation to control the first controller 67 to supply the carbon dioxide gas to the flexiblescope 31 and that to control the pump 72 to supply the air to the flexiblescope 31.

The gas insufflation operations of the second controller 78C will be described in reference to a flowchart shown in FIG. 12.

Figure 12:
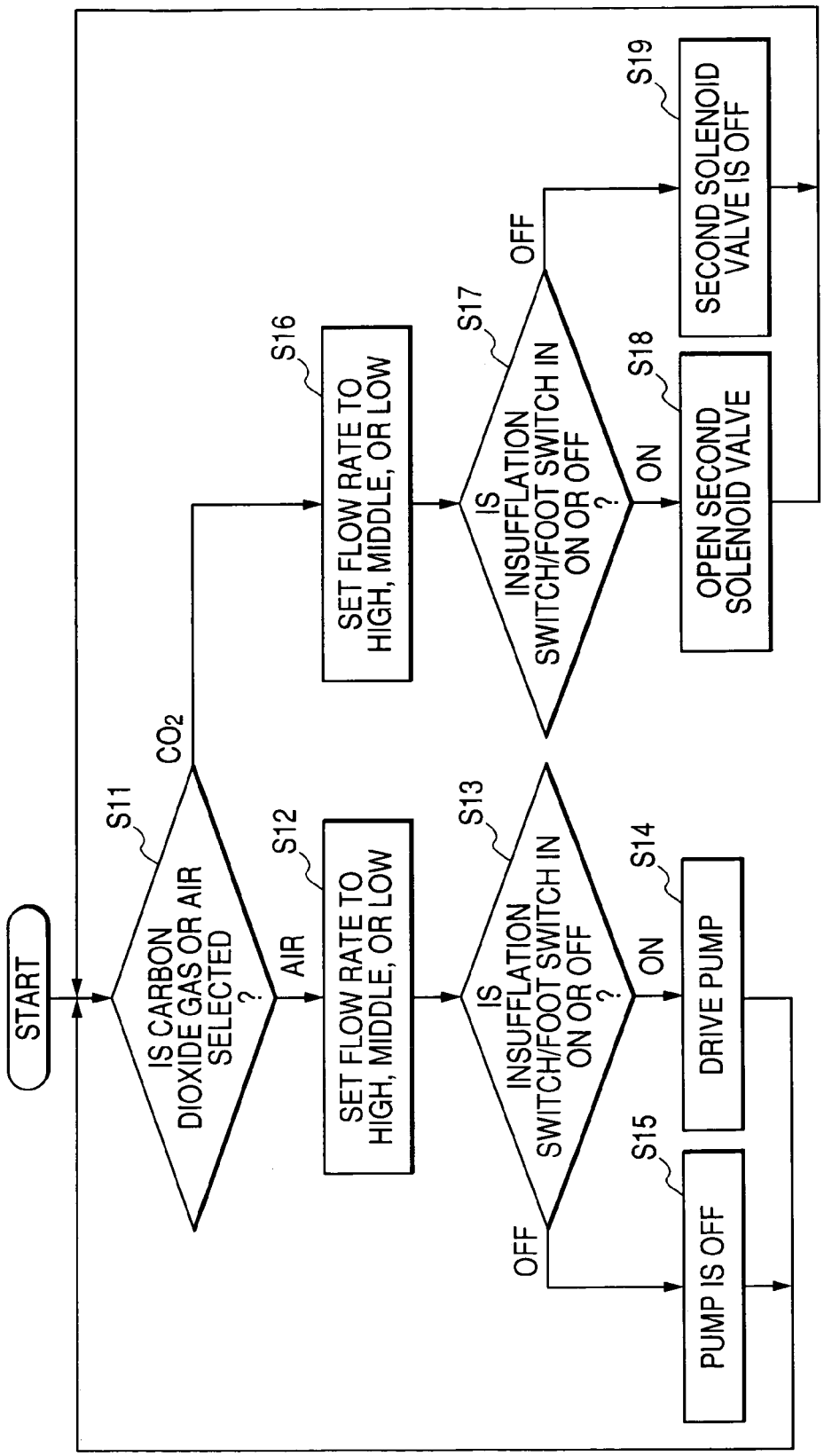
FIG. 12 is a flowchart schematically illustrating an example of operations of a second controller and a first controller illustrated in FIG. 10.

At first, the second controller 78C determines whether the carbon dioxide gas or the air is selected as the supply source to the flexiblescope 31 based on the instruction representing that the selection of any one of the carbon dioxide gas and the air sent from the setting and display circuit 76 (FIG. 12; step S11).

When the instruction represents the selection of the air as the gas-supply source, the determination in step S11 is "AIR", the second controller 78C shifts to step S12. In step S12, the second controller 78C sets, based on the setting information sent from the setting and display circuit 76, the flow-rate of the insufflation gas (air) to the flow-rate setting, that is, any one of the Low range, Middle range, and High range, included in the setting information.

Next, the second controller 78C determines whether at least one of the insufflation switch 82a and the switch portion 44a of the foot switch 44 is in on state (step S13).

When both the insufflation switch 82a and the switch portion 44a of the foot switch 44 are in off state, the second controller 78C keeps the pump 72 off (step S115), returning to the operation in step S11.

In contrast, when the insufflation switch 82a and/or the switch portion 44a of the foot switch 44 is in on state, the second controller 78C shifts to step S14. In step S14, the second controller 78C drives the pump 72 based on the measured result of the third flow-rate sensor 66C to deliver the air with a predetermined pressure such that the flow-rare of the air becomes the flow-rate setting set by the operation in step S12.

The air fed out from the pump 72, as shown in FIG. 10, passes through the channel C10, the check valve 73B, the channel C12, the universal cord 72, and the like to be supplied to the flexiblescope 31. The air is guided by the flexiblescope 31 to be insufflated into the lumen BC, causing the lumen BC to distend.

The second controller 78C repeatedly executes the operations in step S11 to S14 until at least one of the insufflation switch 82a and the switch portion 44a of the foot switch 44 is turned off. When at least one of the insufflation switch 82a and the switch portion 44a of the foot switch 44 is turned off, the second controller 78C controls the pump 72 to stop the delivery of air (step S15), returning to the operation in step S11.

In contrast, when the instruction represents the selection of the carbon dioxide gas as the supply source, the determination in step S11 is "$CO_2$", the second controller 78C shifts to step S16. In step S16, the second controller 78C sets, based on the setting information sent from the setting and display circuit 76, the flow-rate of the insufflation gas (carbon dioxide gas) to the flow-rate setting, that is, any one of the Low range, Middle range, and High range, included in the setting information.

Next, the second controller 78C determines whether at least one of the insufflation switch 82a and the switch portion 44a of the foot switch 44 is in on state (step S17).

When both the insufflation switch 82a and the switch portion 44a of the foot switch 44 are in off state, the second controller 78C communicates with the first controller 67 via the communication cable 47 to keep the second solenoid valve 64B of the gas supply apparatus 41C closed (step S19), returning to the operation in step S11.

In contrast, when the insufflation switch 82a and/or the switch portion 44a of the foot switch 44 is in on state, the second controller 78C communicates with the first controller 67 via the communication cable 47 to open the second electropneumatic proportional valve 63B and the second solenoid valve 64B of the gas supply apparatus 41C (step S18).

The first controller 67 of the gas supply apparatus 41C controls the opening of the valve 63B so as to regulate the flow-rate of the carbon dioxide gas to the flow-rate setting set by the operation in step S16.

This results in that the carbon dioxide gas passes through the second electropneumatic valve 63B so that the flow-rate thereof is regulated to the flow-rate setting set by the operation in step S16. The carbon dioxide gas with its flow-rate regulated is guided to the second $CO_2$ supply path DC2 directing it into the lumen BC.

That is, the carbon dioxide gas passes through the second solenoid valve 64B, the seventh delivery channel C7, the second flow-rate sensor 66B, the eighth delivery channel C8, the lumen adapter 41b, and the lumen tube 45b to enter into the second light source 32C through the inlet adapter 74.

Under such a gas supply state, the measured result of the second flow-rate sensor 66B is sent to the first controller 67.

The first controller 67 adjusts the opening of the second electropneumatic proportional valve 63B so as to regulate the pressure of the carbon dioxide gas flowing therethrough within the corresponding appropriate range of 0 to 500 mmHg or thereabout set forth above. Simultaneously, the first controller 67 adjusts the opening of the second electropneumatic proportional valve 63B to regulate the flow-rate of it to the flow-rate setting set by the operation in step S16.

The carbon dioxide gas entered into the second light source 32C, as shown in FIG. 10, passes through the channel C11, the check valve 73A, the channel C12, the universal cord 72, and the like to be supplied to the flexiblescope 31. The carbon dioxide as is guided by the flexiblescope 31 to be insufflated into the lumen BC, causing the lumen BC to distend.

The second controller 78C repeatedly executes the operations in step S11, and step S16 to step S18 until at least one of the insufflation switch 82a and the switch portion 44a of the foot switch 44 is turned off. When at least one of the insufflation switch 82a and the switch portion 44a of the foot switch 44 is turned off, the second controller 78C causes the first controller 67 to close the second electropneumatic proportional valve 63B and the second solenoid valve 64B. This stops the $CO_2$ insufflation through the second $CO_2$ delivery path DC2 (step S19). Thereafter, the second controller 78C returns to the operation in step S111.

As described above, in the surgical system 1 with the gas supply system 4C according to the second embodiment, it is possible to control the flow-rate of the insufflation gas supplied into the lumen BC to the flow-rate setting set by the operator, in addition to the effects described in the first embodiment. This enhances the operability of gas insufflation of the lumen BC.

Incidentally, the described operator's settings for gas insufflation of the lumen BC with the front panel 32a of the second light source 32C can be carried out with the center operation panel electrically connected to the system controller 5.

Figure 13:
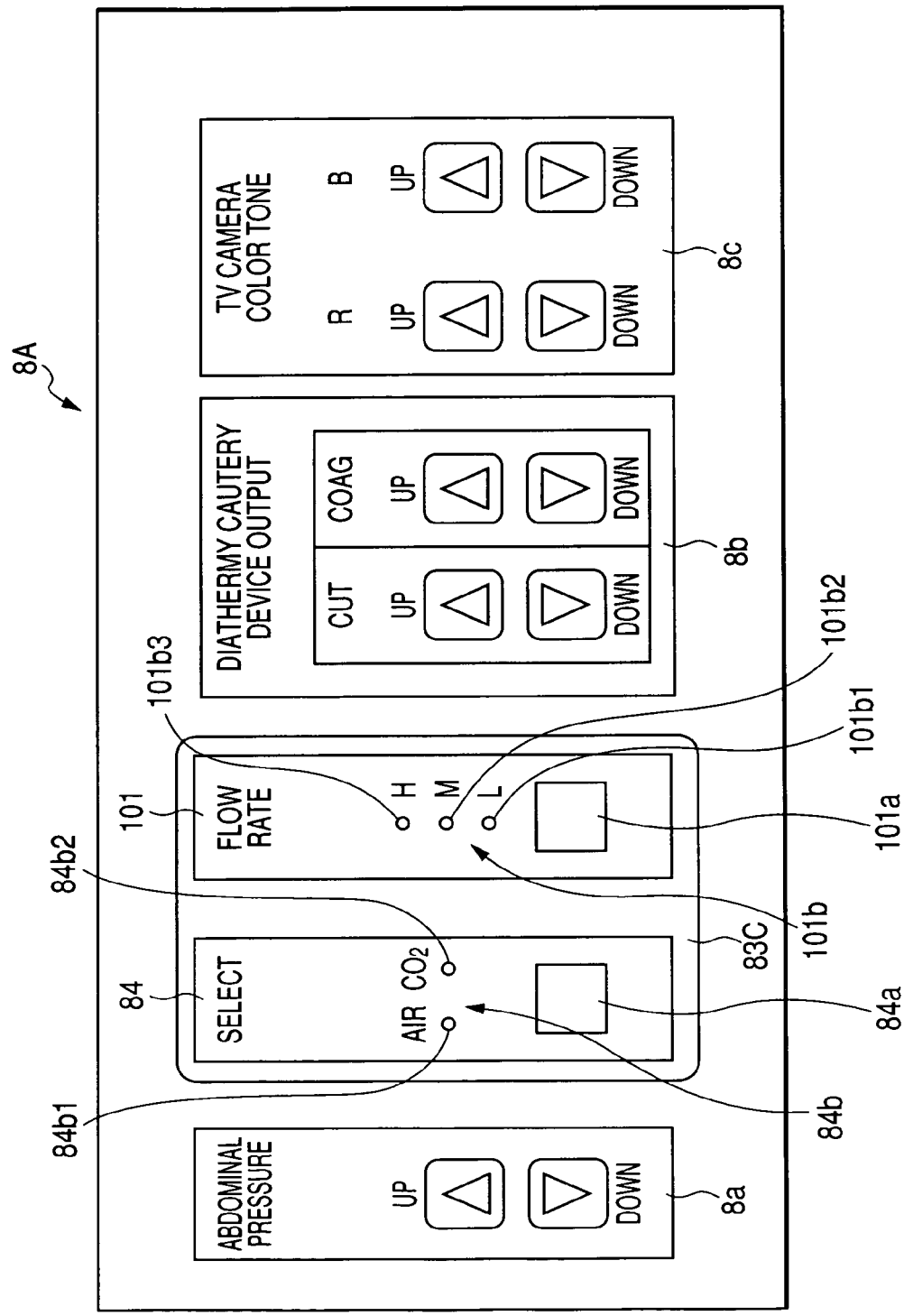
FIG. 13 is a view schematically illustrating a configuration example of a center operation panel of a modification of the gas supply system according to the second embodiment.

As illustrated in FIG. 13, a center operation panel 8A according to a modification of the second embodiment is provided with an operable setting section 8a that allows the operator to adjust the pressure of carbon dioxide gas supplied into the abdominal cavity AC from the gas supply apparatus 41 or 41C.

The center operation panel 8A is provided with the lumen insufflation setting section 83C, which is substantially identical with that provided in the operation panel 75C. The center operation panel 8A is provided with an electric scalpel setting section 8b that allows the operator to adjust an output value of the electric scalpel device 12.

The center operation panel 8A is provided with a TV-camera color tone setting section 8c that allows the operator to control color tones of the first and second CCUs 23 and 33. The center operation panel 8A can be provided with a video mixer setting section that permits the operator to send instructions to the system controller 5 for selectively switching to display the first image (the endoscopic image of the rigid-scope 21) and the second image (the endoscope image of the flexiblescope 31) on the monitor 6. The center operation panel 8A can be provided with a VTR setting section that permits the operator to send instructions to the system controller 5 for making the VTR start recording the first image and/or second image on a video tape or for stopping the record of the first image and/or second image thereon.

In the gas supply apparatus 4C according to the modification, the operator operates the lumen insufflation setting section 83C of the center operation panel 8A in place of the operation panel 75C to send the setting information to the second controller 78C of the second light source 32C through the system controller 5. This results in that the gas supply apparatus 4C of the modification can obtain the effects, which have been already described in the second embodiment.

As another modification of the second light source described in the second embodiment, the operation panel 75C of the second light source 32C can be provided with a low $CO_2$ warning section 102 for the $CO_2$ bottle 42 of the gas supply apparatus 41C.

Figure 14:
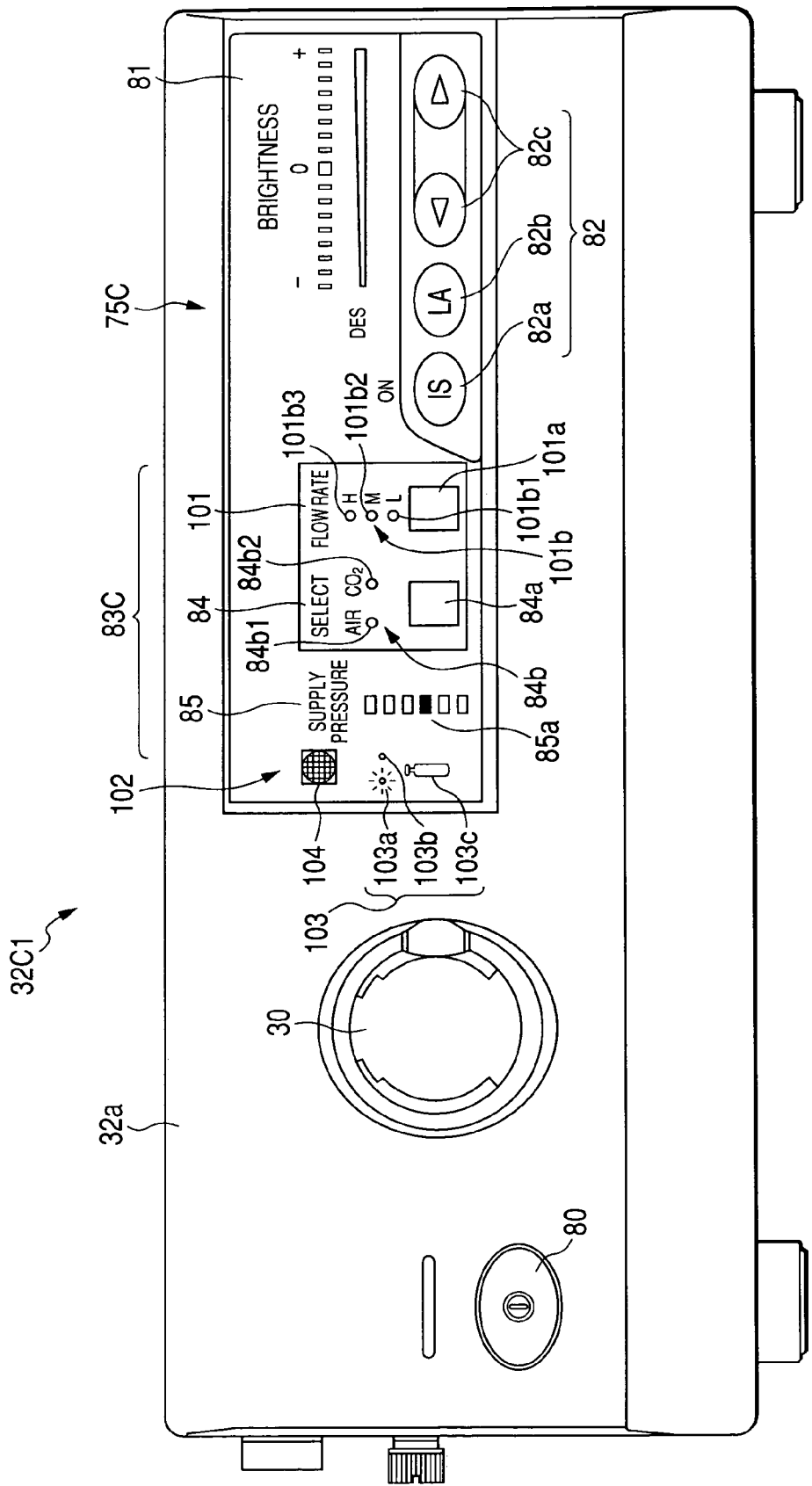
FIG. 14 is a view schematically illustrating a configuration example of a front panel of a second light source of another modification of the gas supply system according to the second embodiment.

Specifically, as illustrated in FIG. 14, an operation panel 75D of a second light source 32C1 according to the modification of the second embodiment is provided with the low $CO_2$ warning section 102 for the $CO_2$ bottle 42 of the gas supply apparatus 41C.

The low $CO_2$ warning section 102 includes a warning LED section 103 and a warning speaker 104. The warning speaker 104 is electrically connected to the second controller 78C through the setting and display circuit 76C.

The warning LED section 103 is composed of a green LED 103a and a red LED 103b, which are electrically connected to the second controller 78C through the setting and display circuit 76C.

In this modification, the second controller 78C periodically communicates with the first controller 67 to periodically obtain remaining amount information indicative of the amount of carbon dioxide gas available in the $CO_2$ bottle 42.

Specifically, when determining that the amount of carbon dioxide gas available in the $CO_2$ bottle 42 reaches a predetermined one based on the remaining amount information, the second controller 78C and the setting and display circuit 76C allow the warning speaker 104 to generate an alarm. In addition, when determining that the amount of carbon dioxide gas available in the $CO_2$ bottle 42 reaches the predetermined one based on the remaining amount information, the second controller 78C and the setting and display circuit 76C allow the green LED 103*a* to turn on. If determining that the $CO_2$ bottle 42 approximately gets empty based on the remaining amount information, the second controller 78C and the setting and display circuit 76C allow the red LED 103*b* to turn on. Incidentally, reference numeral 103*c* represents a character indicative of the low $CO_2$ warning section 102.

In the second light source 32C1 according to the modification, when the amount of carbon dioxide gas available in the $CO_2$ bottle 42 reaches the predetermined one, the green LED 103*a* is turned on and the alarm is outputted from the warning speaker 104. Thereafter, when the $CO_2$ bottle 42 approximately gets empty, the red LED 103*b* is turned on.

The lighting of the green LED 103*a* and/or the alarm outputted from the speaker allow the operator to recognize that the amount of carbon dioxide gas available in the $CO_2$ bottle 42 reaches the predetermined one. This enables the operator to prepare an exchange of the bottle 42 in advance. This makes it possible to prevent the operator from recognizing the amount of carbon dioxide gas available in the $CO_2$ bottle 42 reaches the predetermined one after the lumen BC has shrunk due to non-supply of the carbon dioxide gas into the lumen BC.

Third Embodiment

A gas supply system 4E according to a third embodiment of the present invention is provided with a connection adapter 110 attached to a second light source 32E of the gas supply system 41E. The gas supply system 4D is configured to supply the carbon dioxide gas fed from a gas supply apparatus 41E of the system 4E into the flexiblescope 31.

Incidentally, to elements of the gas supply system 4E, which are substantially identical to those of the first embodiment described above, the same reference characters of the gas supply system 4 (see FIG. 3) are assigned, and therefore, descriptions thereabout are omitted or simplified.

Figure 15:
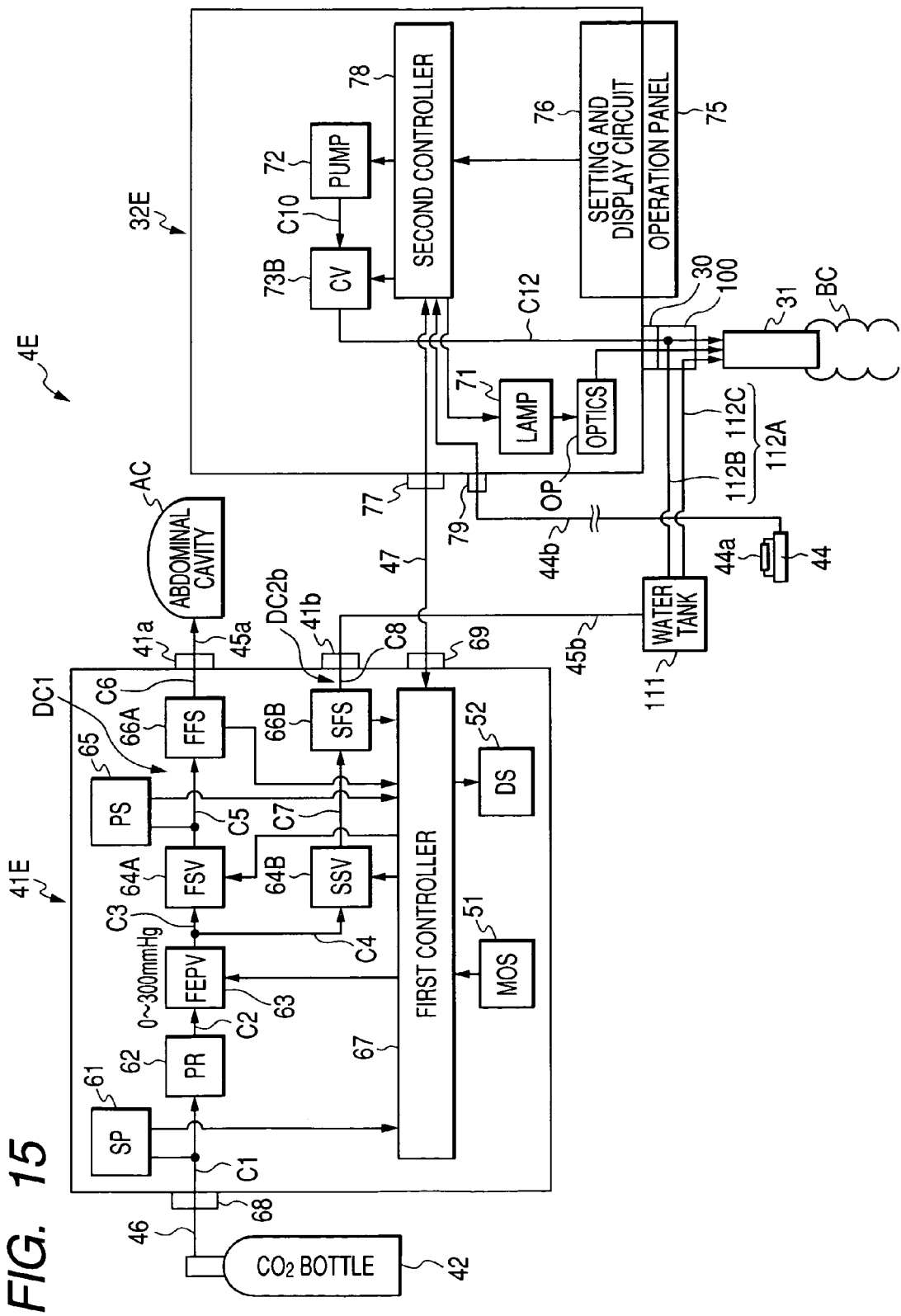
FIG. 15 is a block diagram illustrating a schematic structure of a gas supply system according to a third embodiment of the present invention.
Figure 16:
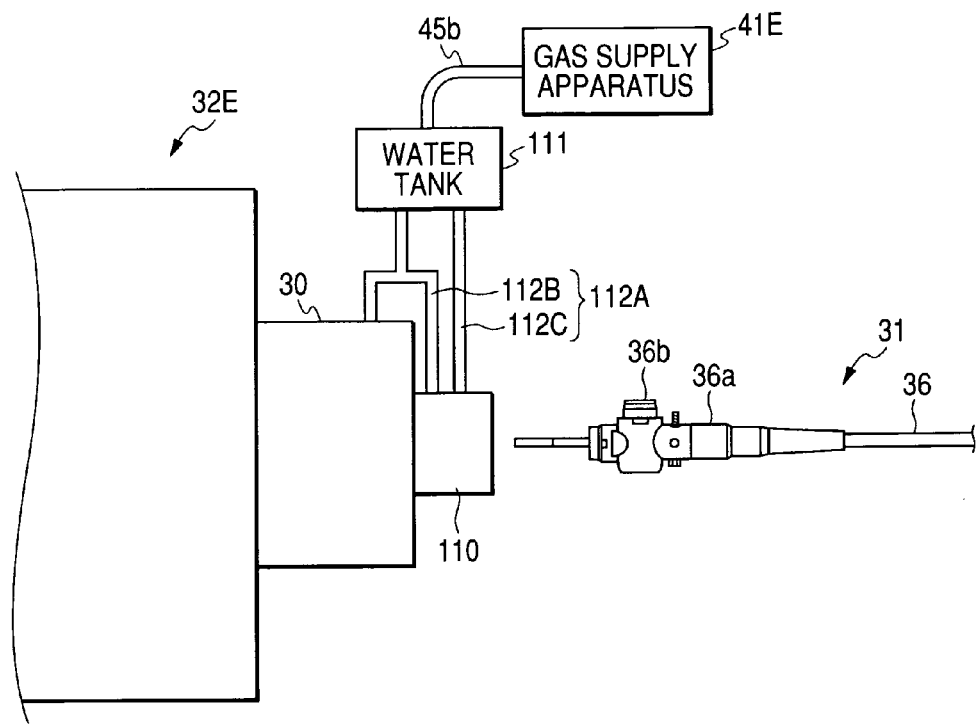
FIG. 16 is an enlarged view of a portion of the gas supply system according to the third embodiment.

As illustrated in FIGS. 15 and 16, the gas supply system 4E according to the third embodiment is provided with the connection adapter 110 detachably coupled to the connector 30 of the second light source 32E. The gas supply system 4E is also provided with a water tank 111 detachably coupled to the connection adapter 110.

Specifically, the second light source 32E according to the third embodiment is equipped with the connection adapter 110 and the water tank 111 in place of the $CO_2$ inlet adapter 74, the channel C11 coupled thereto, and the check valve 73A provided in the channel C11 in the second light source 32 according to the first embodiment. These elements 74, C11, and 73A constitute a $CO_2$ path from the gas supply apparatus 41 to the second light source 32.

Other elements of the gas supply system 4E are substantially identical to those of the gas supply system 4 according to the first embodiment. Hence, descriptions of the other elements of the gas supply system 4E according to the third embodiment to which the same reference characters of the corresponding elements of the gas supply system 4 (see FIG. 3) are assigned are omitted or simplified.

Figure 17:
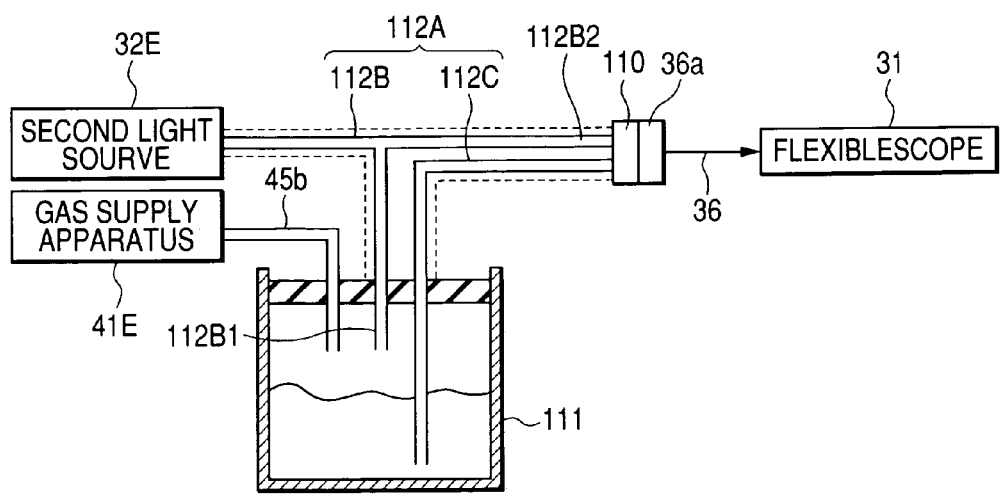
FIG. 17 is a partially enlarged and sectional view of the portion of the gas supply system illustrated in FIG. 16.

As shown in FIGS. 15 to 17, the connection adapter 110 is communicably coupled to the water tank 111 through gas and water supply tubes 112A. The one end of the lumen tube 45*b* is coupled to the second adapter 41*b* of the gas supply apparatus 41E, and the other thereof is coupled to the water tank 111.

The lumen tube 45*b* is configured to be communicated with the universal cord 36 through the water tank 111, the gas and water supply tubes 112A, the connection adapter 110, and the light source connector 36*a*. This allows the carbon dioxide gas supplied from the gas supply apparatus 41E to be insufflated into the lumen BC.

As a liquid, for example, distilled water is accumulated in the water tank 111. One opening end of the gas and water supply tubes 112A and the one end (opening end) of the lumen tube 45*b* are communicated with the interior of the water tank 111.

The gas supply tubes 112A include a branch gas tube 112B and a water tube 112C. One end of the branch gas tube 112B is coupled to the connector 30 of the second light source 32E, and the other branched ends 112B1 and 112B2 thereof are coupled to the water tank 111 and the connection adapter 110, respectively. One end of the water tube 112C is configured to be soaked in the distilled water in the water tank 111, and the other end thereof is coupled to the connection adapter 110.

Figure 18:
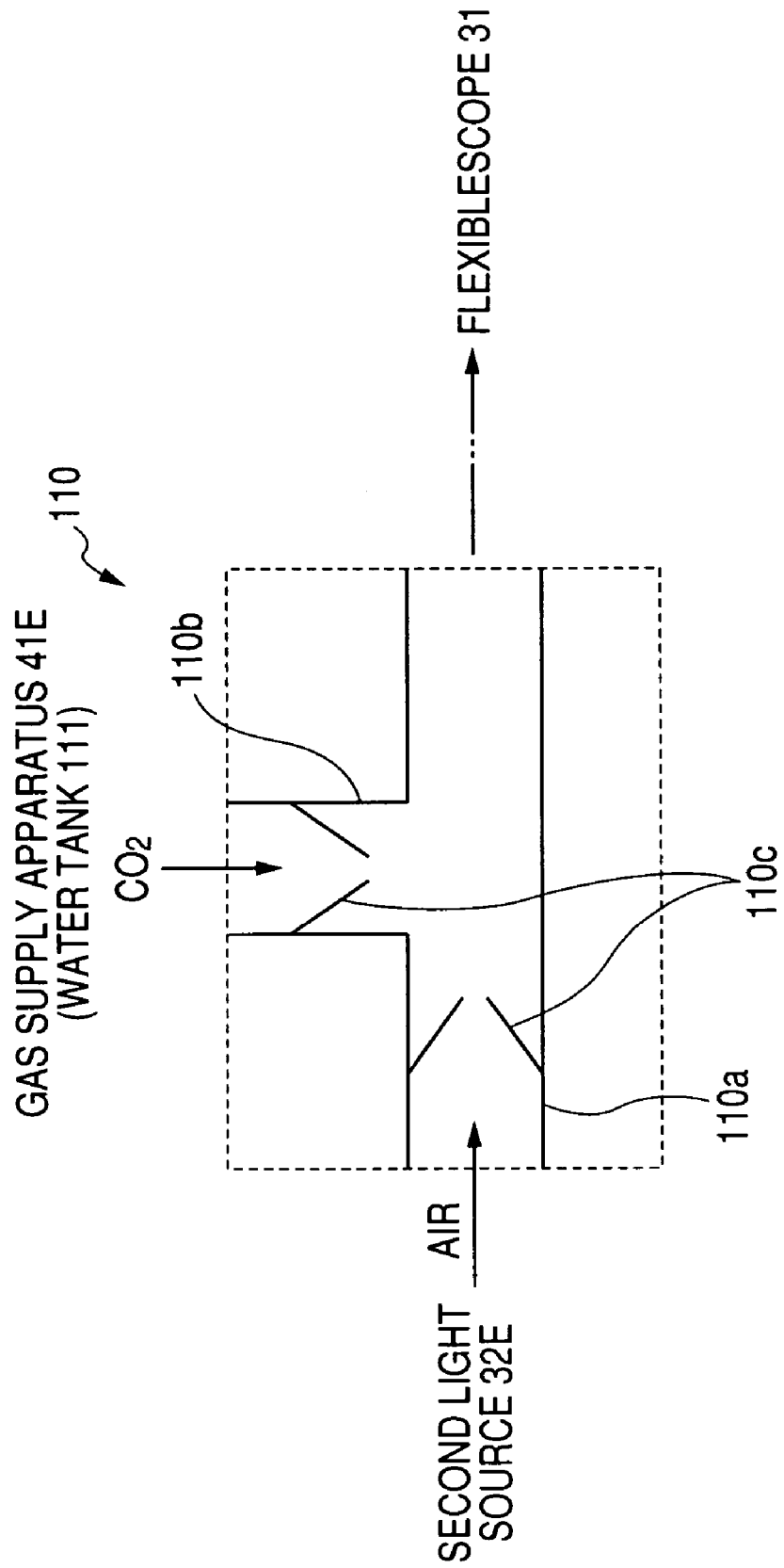
FIG. 18 is a schematically enlarged view of a connection adapter illustrated in FIGS. 16 and 17.

In addition, as illustrated in FIG. 18, the connection adapter 110 is composed of an air channel 110*a* that allows the air supplied from the second light source 32E to pass therethrough. The connection adapter 110 is composed of a $CO_2$ channel 110*b* communicably coupled to the air channel 110*a*. The $CO_2$ channel 110*b* allows the carbon dioxide gas supplied from the gas supply apparatus 41E through the gas tube 112B to pass therethrough.

In addition, the connection adapter 110 is composed of check valves 110*c* provided in the air channel 110*a* and the $CO_2$ channel 110*b*, respectively. The check valves 110*c* are configured to prevent the air and the carbon dioxide gas from flowing back to the pump side and the gas-supply apparatus side, respectively.

One end of the air channel 110*a* is communicably coupled to the gas delivery channel inside the universal cord 36 through the light source connector 36*a*.

When supplying the air into the interior of the flexiblescope 31, as illustrated in FIG. 15, the branch end 112B2 of the branch gas tube 112B is connected to the other end of the air channel 110*a*. In contrast, when supplying the carbon dioxide gas into the interior of the flexiblescope 31, the branch end 112B2 of the branch gas tube 112B is switched to be connected to the $CO_2$ channel 110*b*.

Figure 19:
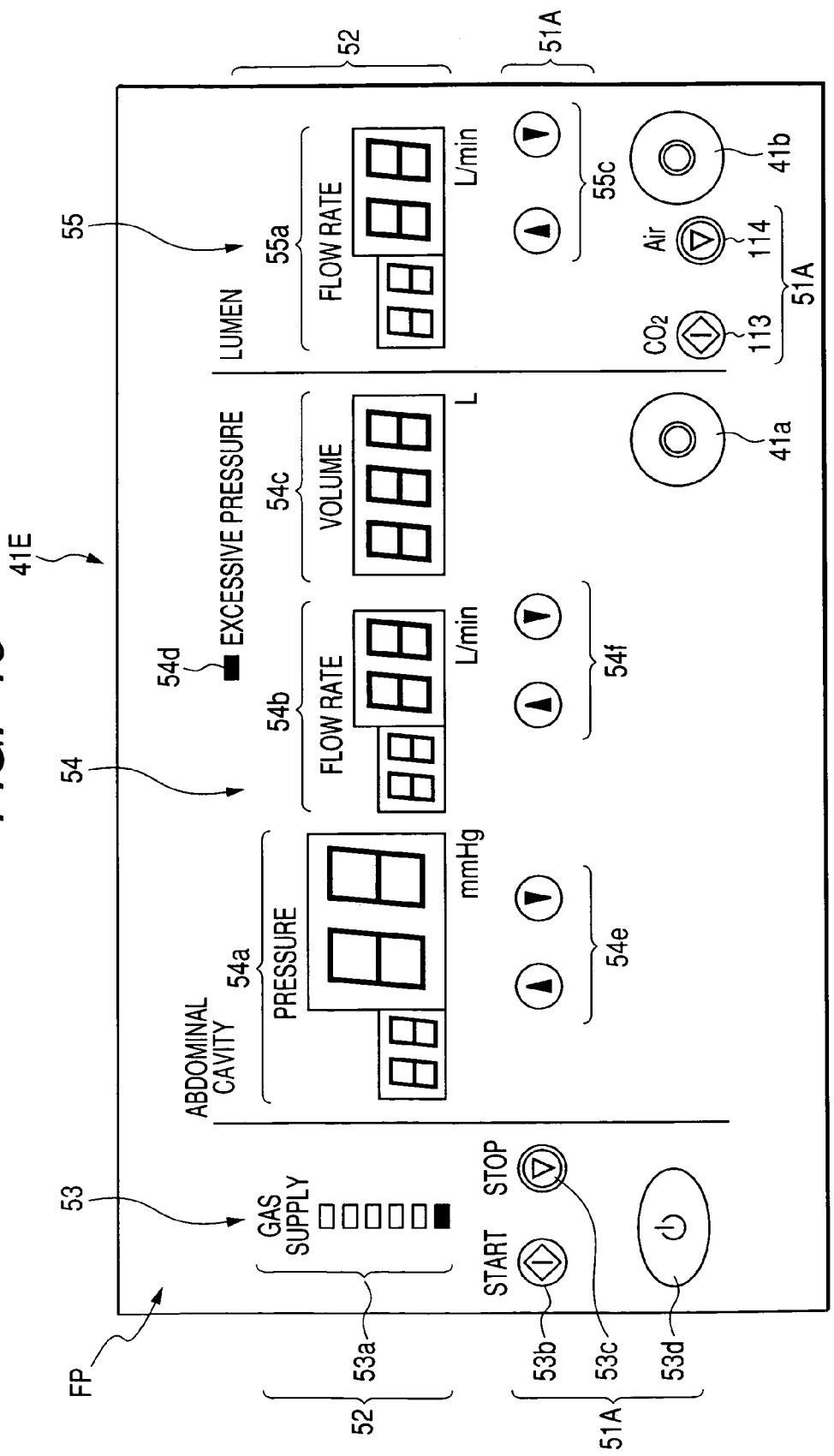
FIG. 19 is a view schematically illustrating a configuration example of a front panel of a second light source illustrated in FIGS. 15 to 17.

In addition, as illustrated in FIG. 19, a manually operable setting section 51A of the front panel FP of the gas supply apparatus 41E according to the third embodiment is provided with a $CO_2$ instruction button 113 and an air instruction button 114, in addition to the structure of the manually operable setting section 51. Each of the switches 113 and 114 is, for example, a graphical toggle switch (on/off switch). Turning on of the $CO_2$ instruction button 113 allows $CO_2$ insufflation to be instructed to the second controller 78 through the first controller 67. In contrast, turning on of the air instruction button 114 permits air insufflation to be instructed to the second controller 78 through the first controller 67.

When both of the instruction buttons 113 and 114 are in off state, the first controller 67 recognizes that it is in the abdominal-cavity insufflation mode.

Specifically, in the gas supply system 4E set forth above, the front panel FP of the gas supply apparatus 41E allows the operator to switch between air insufflation and $CO_2$ insufflation into the flexiblescope 31.

That is, turning on of the $CO_2$ instruction button 113 or the air instruction button 114 by the operator allows the gas supply system 4E to be ready for insufflation of the carbon dioxide gas or the air to the flexiblescope 31. Alternatively, operation of the selection switch 84*a* by the operator allows the gas supply system 4E to be ready for insufflation of the carbon dioxide gas or the air to the flexiblescope 31.

Thereafter, operation of the gas and water supply switch 35a (see FIG. 1) of the flexiblescope 31 by the operator allows the selected insufflation gas (carbon dioxide gas or air) or the distilled water accumulated in the tank 111 to be selectively supplied from the one end of the insertion portion 34 of the flexiblescope 31 into the lumen BC. Specifically, when "water supply" is selected by the gas and water supply switch 35a, the gas delivery channel inside the manipulator 35, which is connected to the gas tube 112B, is configured to be closed.

The carbon dioxide gas fed from the gas supply apparatus 41E into the water tank 111 or the air fed from the second light source 32E thereinto causes pressure in the tank 111 to increase. The increase in pressure in the water tank 111 allows the distilled water accumulated in the tank 111 to flow into the water tube 112C. This results in that the distilled water passes through the connection adapter 110, the light connector 36a, and the gas delivery channel inside the universal cord 36 to be supplied into the lumen BC via the insertion portion 34 of the flexiblescope 31.

In contrast, when "gas supply" is selected by the gas and water supply switch 35a, the gas delivery channel inside the manipulator 35, which is connected to the water tube 112C, is configured to be closed. The carbon dioxide gas fed from the gas supply apparatus 41E into the water tank 111 or the air fed from the second light source 32E thereinto passes through the interior of the tank 111, flowing through the connection adapter 110, the light connector 36a, and the gas delivery channel inside the universal cord 36 to be supplied into the lumen BC via the insertion portion 34 of the flexiblescope 31.

As described above, in the gas supply system 4E according to the third embodiment, providing the connection adapter 110 and the water tank 111 permits the carbon dioxide gas fed from the apparatus 41E and the air fed from the second light source 32E to be easily switched.

Incidentally, in the first to third embodiments and their modifications, the second controller 78 (78C), the setting and display circuit 76, and/or the first controller 67 carry out the operations illustrated in FIG. 5, FIG. 12, and the like, but the system controller 5 can execute them.

In the first to third embodiments and their modifications, the selection switch 84a is provided for switching any one of the carbon dioxide gas and the air to be supplied into the lumen BC. The present invention is, however, not limited to the structure. Specifically, in place of the selection switch 84a, a selection unit manually or remotely operable by the operator can be provided in the gas supply systems according to the first to third embodiments and their modifications. The selection unit is configured to select any one of the carbon dioxide gas and the air to be supplied into the lumen BC based on the manual or remote operation of the selection unit. The selection unit is configured to output instruction to select any one of the carbon dioxide gas and the air to be supplied into the lumen BC to the second controller 78.

In the first to third embodiments and their modifications, the flexiblescope 31 constitutes part of an insufflation-gas delivery path from the gas supply apparatus 41 and the second light source 32 to the lumen BC, but the present invention is not limited to the structure. Specifically, an insufflation-gas delivery path independent of the flexiblescope 31 can be provided in each of the gas supply systems according to the first to third embodiments and their modifications.

In the first to third embodiments and their modifications, the rigidscope and the flexiblescope are used as observation devices for observing the inside of a patient (body), but the present invention is not limited to the structure. Specifically, other types of endoscopes, such as a wireless capsule endoscope or the like, or other observation devices except for endoscopes, each of which is configured to be inserted into the inside of a patient (body), can be used for observing the inside of the patient.

Furthermore, it should be noted that the term "body cavity" means not only a cavity that originally exists in a body (patient), but also a cavity (space) to be artificially formed in the body (patient) with medical instruments.

For example, the term "body cavity" according to the specification includes, as the former means, an abdominal cavity, a lumen including upper alimentary tracts (esophagus, stomach, or the like), lower alimentary tracts (large intestine, small intestine, or the like), a bladder, and a uterus.

In addition, the term "body cavity" according to the specification includes, as the later means, a cavity to secure the field of an endoscope during surgery, such as subcutaneous cavity and the like.

While there has been described what is at present considered to be the embodiment and modifications of the invention, it will be understood that various modifications which are not described yet may be made therein, and it is intended to cover in the appended claims all such modifications as fall within the true spirit and scope of the invention.

What is claimed is:

1. A gas supply system comprising:
a first gas supply unit configured to supply a first gas into a body;
a second gas supply unit configured to supply a second gas into the body;
a selection unit configured to send an instruction to select any one of the first gas and the second gas; and
a controller electrically connected to the first gas supply unit, the second gas supply unit, and the selection unit and operative to control at least one of the first gas supply unit and the second gas supply unit to selectively insufflate any one of the first gas and the second gas into the body based on the instruction sent from the selection unit, the controller operable to control the insufflation such that any one of the first gas and the second gas is provided to at least one cavity in the body to cause the cavity to distend for treatment or diagnosis in the at least one cavity,
wherein the second gas supply unit comprises:
a gas-supply source for the second gas;
a delivery member coupled to the gas-supply source and configured to deliver the second gas into the body, part of the delivery member serving as a gas delivery channel of an observation device, part of the observation device being inserted into the body to observe an interior of the body; and
an illumination light source operable to output illumination light, wherein the second gas supply unit serves as an illumination light supply unit to supply the illumination light outputted from the light source through the delivery member into the observation device, and wherein the illumination light source comprises:
a lamp for outputting the illumination light; and
a light source controller,
wherein the gas-supply source is installed in the illumination light source, and the light source controller is configured to control an amount of the second gas to be supplied from the gas-supply source, and to control an operating state of the lamp.

2. The gas supply system according to claim 1, wherein the gas-supply source is electrically connected to the controller and is configured to be driven based on control of the controller, and the controller drives the gas-supply source to supply the second gas through the delivery member when the instruction is to select the second gas.

3. The gas supply system according to claim 1, wherein the second gas supply unit comprises an opening and closing device connected electrically to the controller and provided in the delivery member to be openable and closable, and the controller closes the opening and closing unit when the instruction is to select the first gas.

4. The gas supply system according to claim 1, wherein the first gas supply unit comprises a delivery member configured to deliver the first gas into the body, and an opening and closing unit connected electrically to the controller and provided in the delivery member to be openable and closable, and the controller closes the opening and closing unit when the instruction is to select the second gas.

5. The gas supply system according to claim 1, further comprising a flow-rate setting unit configured to set a flow-rate setting of at least one of the first gas and the second gas to output first information indicative of the flow-rate setting of at least one of the first gas and the second gas, the flow-rate setting unit being electrically connected to the controller, and the controller controls correspondingly at least one of the first gas supply unit and the second gas supply unit based on the first information to regulate a flow-rate of at least one of the first gas and the second gas.

6. The gas supply system according to claim 5, wherein the first information outputted from the flow-rate setting unit is indicative of the flow-rate setting of the second gas, and the second gas supply unit comprises:
 a gas-supply source electrically connected to the controller and configured to insufflate the second gas based on control of the controller, the gas-supply source allowing regulation of the flow-rate of the second gas based on control of the controller;
 a delivery member coupled to the gas-supply source to deliver the second gas into the body; and
 a flow-rate sensor provided in the delivery member and electrically connected to the controller, the flow-rate sensor measuring the flow-rate of the second gas flowing through the delivery member to output the second information indicative of the measured flow-rate, and
 wherein the controller controls the gas-supply source based on the first information and the second information to regulate the flow-rate of the second gas.

7. The gas supply system according to claim 5, wherein the first information outputted from the flow-rate setting unit is indicative of the flow-rate setting of the first gas, and the first gas supply unit comprises:
 a delivery member configured to deliver the first gas into the body;
 a flow-rate sensor provided in the delivery member and electrically connected to the controller, the flow-rate sensor measuring the flow-rate of the first gas flowing through the delivery member to output a second information indicative of the measured flow-rate; and
 a flow-rate regulating unit provided in the delivery member and electrically connected to the controller, the flow-rate regulating unit being configured to regulate the flow-rate of the first gas flowing through the delivery member, and
 wherein the controller controls the flow-rate regulating unit based on the first information and the second information to regulate the flow-rate of the first gas.

8. The gas supply system according to claim 5, further comprising an operation panel operable by an operator, the flow-rate setting unit being so designed on the operation panel as to allow the operator to set the flow-rate setting of at least one of the first gas and the second gas.

9. The gas supply system according to claim 1, wherein the selection unit includes a selection switch operable by an operator, further comprising an operation panel operable by an operator, the selection switch being so designed on the operation panel as to allow the operator to select any one of the first gas and the second gas.

10. The gas supply system according to claim 9, further comprising a display unit provided on the operation panel and electrically connected to the controller, wherein when any one of the first gas and the second gas is selected by the selection switch, the controller displays gas selection information on the display unit to be visually recognizable by the operator, the gas selection information representing the selected one of the first gas and the second gas.

11. The gas supply system according to claim 9, wherein the operation panel is a panel for manually operating the second gas supply unit.

12. The gas supply system according to claim 9, wherein the operation panel is a panel for manually operating the first gas supply unit.

13. The gas supply system according to claim 1, wherein the first gas supply unit comprises a first delivery member configured to deliver the first gas into the body, and the second gas supply unit comprises:
 a gas-supply source for the second gas; and
 a second delivery member coupled to the gas-supply source to deliver the second gas into the body, and
 wherein the first delivery member and the second delivery member have a common portion.

14. The gas supply system according to claim 13, further comprising a connection adapter provided in the first delivery member and the second delivery member such that the common portion of the first delivery member and the second delivery member is detachable via the connection adapter from the remaining portions of the first delivery member and the second delivery member, and the connection adapter allows the selected one of the first gas and the second gas to be delivered to the common portion of the first delivery member and the second delivery member.

15. The gas supply system according to claim 1, wherein the delivery member is provided with a light-gas guiding path coupling between the observation device and the gas-supply source, the light-gas guiding path guiding;
 the second gas supplied from the gas-supply source into the observation device; and
 the illumination light outputted from the light source into the observation device.

16. The gas supply system according to claim 1, further comprising:
 a cable having one end removably and communicably coupled to the first gas supply unit and a second end removably and communicably coupled to the second gas supply unit.

17. A gas supply system comprising:
 means for supplying a first gas into a body;
 means for supplying a second gas into the body;
 means for sending an instruction to select any one of the first gas and the second gas; and
 means for selectively insufflating any one of the first gas and the second gas into the body based on the instruction sent from the selection means, the means for selectively insufflating operable to control the insufflation such that any one of the first gas and the second gas is provided to at least one cavity in the body to cause the cavity to distend for treatment or diagnosis in the at least one cavity,
 wherein the means for supplying second gas comprises:

a gas-supply source for the second gas;
a delivery member coupled to the gas-supply source and configured to deliver the second gas into the body, part of the delivery member serving as a gas delivery channel of an observation device, part of the observation device being inserted into the body to observe an interior of the body; and
an illumination light source operable to output illumination light,
wherein the means for supplying second gas serves as an illumination light supply unit to supply the illumination light outputted from the light source through the delivery member into the observation device, and, wherein the illumination light source comprises:
a lamp for outputting the illumination light; and
a light source controller,
wherein the gas-supply source is installed in the illumination light source, and the light source controller is configured to control an amount of the second gas to be supplied from the gas-supply source, and to control an operating state of the lamp.

18. The gas supply system according to claim 17, wherein the delivery member is provided with a light-gas guiding path coupling between the observation device and the gas-supply source, the light-gas guiding path guiding;
the second gas supplied from the gas-supply source into the observation device; and
the illumination light outputted from the light source into the observation device.

19. A method of supplying gas into a body, the method comprising:
supplying a first gas into a body;
supplying a second gas into the body;
sending an instruction to select any one of the first gas and the second gas; and
selectively insufflating any one of the first gas and the second gas into the body based on the instruction sent from the sending step, the insufflation of any one of the first gas and the second gas into the body causing at least one cavity in the body to distend for treatment or diagnosis in the at least one cavity,
wherein the second gas supplying includes:
providing a gas-supply source for outputting the second gas, a delivery member, and an illumination light source for outputting illumination light;
coupling the delivery member to the gas-supply source;
delivering the second gas output from the gas-supply source into the body through the delivery member, part of the delivery member serving as a gas delivery channel of an observation device, part of the observation device being inserted into the body to observe an interior of the body; and
supplying the illumination light outputted from the illumination light source through the delivery member into the observation device, and, wherein the illumination light source comprises:
a lamp for outputting the illumination light; and
a light source controller, and
wherein the gas-supply source is installed in the illumination light source, further comprising:
instructing the light source controller to control an amount of the second gas to be supplied from the gas-supply source; and
instructing the light source controller to control an operating state of the lamp.

20. The method of supplying gas according to claim 19, wherein the second gas supplying includes:
providing a light-gas guiding path coupling between the observation device and the gas-supply source, wherein the delivering includes:
guiding the second gas supplied from the gas-supply source into the observation device through the light-gas guiding path; and
providing the illumination light outputted from the light source into the observation device through the light-gas guiding path.

21. A gas supply system comprising:
a first gas supply unit configured to supply a first gas into a body;
a second gas supply unit configured to supply a second gas into the body;
an endoscope coupling configured to supply therethrough one or more of the first gas and the second gas;
a selection unit configured to send an instruction to select any one of the first gas and the second gas to be supplied to the body via the endoscope coupling; and
a controller electrically connected to the first gas supply unit, the second gas supply unit, and the selection unit and operative to control at least one of the first gas supply unit and the second gas supply unit to selectively insufflate any one of the first gas and the second gas into the body based on the instruction sent from the selection unit, the controller operable to control the insufflation such that any one of the first gas and the second gas is provided to at least one cavity in the body to cause the cavity to distend for treatment or diagnosis in the at least one cavity,
wherein the second gas supply unit comprises:
a gas-supply source for the second gas;
a delivery member coupled to the gas-supply source and the endoscope coupling and configured to deliver the second gas into the body, part of the delivery member serving as a gas delivery channel of an endoscope, part of the endoscope being inserted into the body to observe an interior of the body; and
an illumination light source operable to output illumination light, the second gas supply unit serving as an illumination light supply unit to supply the illumination light outputted from the illumination light source through the delivery member into the endoscope, and wherein the illumination light source comprises:
a lamp for outputting the illumination light; and
a light source controller,
wherein the gas-supply source is installed in the illumination light source, and the light source controller is configured to control an amount of the second gas to be supplied from the gas supply source, and to control an operating state of the lamp.

22. The gas supply system according to claim 21, wherein the delivery member is provided with a light-gas guiding path coupling between the observation device and the gas-supply source, the light-gas guiding path guiding;
the second gas supplied from the gas-supply source into the observation device; and
the illumination light outputted from the light source into the observation device.

23. A method of supplying gas via an endoscope coupling into a body, the method comprising:
supplying a first gas into a body via the endoscope coupling;
supplying a second gas into the body via the endoscope coupling;

sending an instruction to select any one of the first gas and the second gas to be supplied via the endoscope coupling; and selectively insufflating any one of the first gas and the second gas into the body based on the instruction sent from the sending step, the insufflation of any one of the first gas and the second gas into the body causing at least one cavity in the body to distend for treatment or diagnosis in the at least one cavity, wherein the supplying of the second gas includes:

providing a gas-supply source for outputting the second gas, a delivery member, and an illumination light source for outputting illumination light;

coupling the delivery member to the gas-supply source and the endoscope coupling;

delivering the second gas output from the gas-supply source into the body through the delivery member, part of the delivery member serving as a gas delivery channel of an endoscope, part of the endoscope being inserted into the body to observe an interior of the body; and supplying the illumination light outputted from the illumination light source through the delivery member into the endoscope via the endoscope, and wherein the illumination light source comprises:

a lamp for outputting the illumination light; and a light source controller, and wherein the gas-supply source is installed in the illumination light source, the method further comprising:

instructing the light source controller to control an amount of the second gas to be supplied from the gas-supply source; and instructing the light source controller to control an operating state of the lamp.

24. A method of supplying gas according to claim 23, wherein the supplying of the second gas includes:

providing a light-gas guiding path coupling between the observation device and the gas-supply source, wherein the delivering includes:

guiding the second gas supplied from the gas-supply source into the observation device through the light-gas guiding path; and the illumination light outputted from the light source into the observation device through the light-gas guiding path.

* * * * *